United States Patent
Kwon et al.

(10) Patent No.: US 10,569,194 B2
(45) Date of Patent: Feb. 25, 2020

(54) LUTERION AND SEPARATING AND CULTURING METHODS FOR SAME

(71) Applicant: LUTERION CO., LTD., Gyeonggi-do (KR)

(72) Inventors: Young Ah Kwon, Seoul (KR); Won Cheol Choi, Incheon (KR); Suk Hoon Choi, Seoul (KR); Chang Hoon Choi, Seoul (KR)

(73) Assignee: LUTERION CO., LTD., Gyeonggi-Do (KR)

( * ) Notice: Subject to any disclaimer, the term of this patent is extended or adjusted under 35 U.S.C. 154(b) by 76 days.

(21) Appl. No.: 15/542,026

(22) PCT Filed: Jan. 6, 2016

(86) PCT No.: PCT/KR2016/000110
§ 371 (c)(1),
(2) Date: Jul. 6, 2017

(87) PCT Pub. No.: WO2016/111552
PCT Pub. Date: Jul. 14, 2016

(65) Prior Publication Data
US 2017/0361243 A1    Dec. 21, 2017

(30) Foreign Application Priority Data

Jan. 6, 2015 (KR) .................. 10-2015-0001195
Jan. 12, 2015 (KR) .................. 10-2015-0004288

(51) Int. Cl.
*A61K 36/00* (2006.01)
*B01D 3/02* (2006.01)
(Continued)

(52) U.S. Cl.
CPC .......... *B01D 11/0296* (2013.01); *A61K 36/00* (2013.01); *B01D 3/02* (2013.01);
(Continued)

(58) Field of Classification Search
CPC .......... B01D 11/0296; B01D 21/262; B01D 61/027; B01D 36/045; B01D 2311/02;
(Continued)

(56) References Cited

U.S. PATENT DOCUMENTS 6,291,203 B1    9/2001 Poot et al.
7,407,800 B1    8/2008 Benton et al.
(Continued)

FOREIGN PATENT DOCUMENTS

JP    10-117766 A    5/1998
JP    2016-526688 A    9/2016
(Continued)

OTHER PUBLICATIONS

Eriksson, M., et al., "Isolation, Purification, and Characterization of Mitochondria from Chlamydomonas reinhardtii", "Plant Physiol.", Feb. 1, 1995, pp. 479-483, vol. 107, No. 2, Publisher: www.plantphysiol.org.

(Continued)

*Primary Examiner* — Joseph W Drodge
(74) *Attorney, Agent, or Firm* — Hultquist, PLLC; Steven J. Hultquist

(57) ABSTRACT

The present disclosure relates to luterion, which is a mitochondrial-like micro-material, and separating and culturing methods for same and, more particularly, to a method for separating luterion by means of a filter having a pore of a particular size, luterion which is separated by means of the method thereof and has unique properties, and a culturing method for proliferation of the luterion.

14 Claims, 24 Drawing Sheets

(51) Int. Cl.
*B01D 11/02* (2006.01)
*B01D 21/26* (2006.01)
*B01D 36/04* (2006.01)
*B01D 61/02* (2006.01)
*C12N 5/04* (2006.01)
*C12N 15/11* (2006.01)
*C12N 15/113* (2010.01)

(52) U.S. Cl.
CPC ......... *B01D 21/262* (2013.01); *B01D 36/045* (2013.01); *B01D 61/027* (2013.01); *C12N 5/04* (2013.01); *C12N 15/113* (2013.01); *B01D 2201/184* (2013.01); *B01D 2311/02* (2013.01)

(58) Field of Classification Search
CPC ............ B01D 2201/184; B01D 5/0057; B01D 5/0069; B01D 5/0072; B01D 5/0075; B01D 11/028; B01D 11/0288; B01D 11/0292; B01D 61/10; B01D 61/20; B01D 2311/06; B01D 2311/2673; B01D 2311/2676; B01D 2311/2688; B01D 2311/2649; B01D 3/02; C12N 5/04; C12N 15/113; C12N 5/0025; B03C 1/32; B04B 5/00; G01N 33/5097; A61K 36/00; A61K 2236/30; A61K 2236/31; A61K 2236/39; A61K 2236/50; A61K 2236/53; A61K 2236/55
USPC ........ 210/640, 650, 651, 774, 787; 424/725, 424/777; 435/173.9, 261
See application file for complete search history.

(56) References Cited

U.S. PATENT DOCUMENTS

| | | | | |
|---|---|---|---|---|
| 2002/0006444 A1* | 1/2002 | Konishi | ............... | A61K 36/00 424/725 |
| 2004/0071792 A1* | 4/2004 | Lee | ............... | A61K 36/532 424/725 |
| 2004/0156920 A1* | 8/2004 | Kane | ............... | A01N 65/00 424/725 |
| 2005/0089499 A1* | 4/2005 | Moussou | ............... | A61K 8/97 424/74 |
| 2006/0153860 A1* | 7/2006 | Cho | ............... | C07K 14/195 424/185.1 |
| 2007/0122492 A1* | 5/2007 | Behr | ............... | A61Q 17/04 424/725 |
| 2008/0125320 A1* | 5/2008 | Coats | ............... | A01N 3/00 504/116.1 |
| 2008/0318790 A1* | 12/2008 | Ebneth | ............... | C07K 14/415 504/307 |
| 2011/0293754 A1* | 12/2011 | Lee | ............... | A61K 36/232 424/728 |
| 2013/0224181 A1* | 8/2013 | Ma | ............... | A61K 8/97 424/115 |
| 2013/0280320 A1* | 10/2013 | Mompon | ............... | A23F 3/14 424/443 |
| 2014/0143906 A1* | 5/2014 | Chen | ............... | C12N 15/8218 800/279 |
| 2014/0314889 A1* | 10/2014 | Duttaroy | ............... | A61K 36/185 424/777 |
| 2015/0173883 A1* | 6/2015 | Ingber | ............... | C09D 5/1662 435/287.2 |

FOREIGN PATENT DOCUMENTS

| | | |
|---|---|---|
| JP | 2017-510248 A | 4/2017 |
| JP | 2018-502152 A | 1/2018 |
| KR | 10-2006-0094211 A | 8/2006 |
| KR | 10-2012-0002942 A | 1/2012 |
| KR | 10-2012-0014014 A | 2/2012 |
| KR | 10-2016-0084820 A | 7/2016 |
| WO | 2009100029 A1 | 8/2009 |
| WO | 2009114700 A2 | 9/2009 |
| WO | 2010039886 A1 | 4/2010 |
| WO | 2013035101 A1 | 3/2013 |
| WO | 2015005553 A1 | 1/2015 |
| WO | 2015108246 A1 | 7/2015 |
| WO | 2015108342 A1 | 7/2015 |

OTHER PUBLICATIONS

Holger, E., et al., "Free-flow electrophoresis for purification of plant mitochondria by surface charge", "The Plant Journal", Nov. 1, 2007, pp. 583-594, vol. 52, No. 3, Publisher: Blackwell Publishing Ltd.

Japazi, A., et al., "High Yields of Hydrogen Production Induced by Meta-Substituted Dichlorophenols Biodegradation from the Green Alga Scenedesmus obliquus", "Plos One", Nov. 7, 2012, pp. e49037, vol. 7, No. 11, Publisher: journal.pone.

Lee, Y., et al., "Exosomes and microvesicles: extracellular vesicles for genetic information transfer and gene therapy", "Human Molecular Genetics", Aug. 7, 2012, pp. R125-R134, vol. 21, No. 1.

* cited by examiner

Life Cycling A

Normal (Fission)

Life Cycling B

Abnormal (Fusion or Coagulation)

Oral Gavage

Organs: 1) Heart / 2) Lung / 3) Spleen / 4) Liver / 5) Pancreas / 6) Kidney
// Testis (except control) // 7) Stomach / 8) Intestine (appendix)

LUTERION AND SEPARATING AND CULTURING METHODS FOR SAME

CROSS-REFERENCE TO RELATED APPLICATIONS

This application is a U.S. national phase under the provisions of 35 U.S.C. § 371 of International Patent Application No. PCT/KR2016/000110 filed Jan. 6, 2016, which in turn claims priority of Korean Patent Application No. 10-2015-0001195 filed Jan. 6, 2015 and Korean Patent Application No. 10-2015-0004288 filed Jan. 12, 2015. The disclosures of such international patent application and Korean priority patent applications are hereby incorporated herein by reference in their respective entireties, for all purposes.

BACKGROUND

Field

The present disclosure relates to luterion, which is a mitochondrion-like micro-material, and methods of separating and culturing the same and more particularly, to a method of separating the luterion using a filter having a pore with a particular size, and a method of culturing and proliferating of the isolated luterion collected from such filtration.

Description of the Related Art

The inventors of the present application developed a method for effectively separating luterial, a micro-material present in body fluids discharged from a patient or a normal person, and clarified the characteristics of the separated luterial to file a patent application on May 9, 2014 (See WO2015/108246). Further, it has been discovered that diagnosis and prediction of diseases can be made by observing the characteristics of the micro-material present in the body fluids pre-discharged from patients, and the patent application was filed on Jan. 14, 2014 (See WO2015/005553).

Such luterial (1) is a cell or cell analogue with intermediate-stage fusion characteristics between prokaryotic and eukaryotic cells; (2) is present in body fluids such as blood, semen, serous fluid, saliva, and cytosol; (3) exhibits a positive chromogenic reaction for Janus green B, Acridine orange, and Rhodamine 123 in the immunofluorescence test; (4) exhibits expression characteristics of genes derived from beta-proteobacteria and gamma-proteobacteria at the optimum environment (pH 7.2-7.4) and has a size of 30 nm to 800 nm; (5) in the acidified environment: exhibits expression characteristics of genes not only derived from beta-proteobacteria and gamma-proteobacteria but also from eukaryotic cells; expresses genes that are mainly homologous to sterptophyta genes; and has enlarges its size from 400 nm or more to 2000 nm or more; (6) is involved in ATP production at the normal condition; and (7) is a cell or cell analogue different from mitochondria and completely different from exosome.

The luterial was found mainly in the blood of animals including humans. Meanwhile, it was confirmed that luterion, a micro material so named to differentiate from from luterial, also exists in plants or foods and that it has similar structures and functions to the luterial.

Under these technical backgrounds, the inventors of the present application have found that, as a result of intensive efforts to effectively isolate and cultivate the luterion so as to be clinically applicable, the present inventors have succeeded in collecting vaporized gas generated by adding a solvent to a plant or food and boiling it. Thereafter, the luterion contained in the vaporized gas can be effectively isolated through filtering and centrifugation, and the luterion separated therefrom can be cultured in a specific condition and a medium, thereby completing the present disclosure.

SUMMARY

An object of the present disclosure is to provide luterion.

Another object of the present disclosure is to provide a method of effectively separating the luterion for clinical application using a filter with a specific pore size.

Still another object of the present disclosure is to provide a method for effectively culturing the luterion.

In order to achieve the above objects, the present disclosure provides the luterion having at least one characteristic selected from the following of:
(a) in a circular or oval shape with a size of 50 nm to 800 nm and having motility
(b) having a nucleic acid;
(c) showing a similar reaction to mitochondria upon immunochemical fluorescence staining;
(d) indicating fusion and/or fission ecological form;
(e) maturing to a size of up to 500 nm in the absence of fusion, maturing into pseudo-mitochondria containing DNA, and showing a mitochondria-like structure on an image obtained by a scanning electron microscope (SEM) or transmission electron microscope (TEM);
(f) showing light reaction different from the exosome
(g) undergoing fission upon IR irradiation or pressurization;
(h) expressing CD332, CD133, CD73 or CD39 as a surface antigen;
(i) showing autofluorescence;
(j) producing ATP at a size of 400 nm or less;
(k) double membrane or multi membrane structure;
(l) having adherence;
(m) inhibiting telomerase activity of cancer cells;
(n) promoting telomerase activity of normal cells;
(o) having cell permeability; and
(p) having bloodbrain barrier (BBB) permeability.

The present disclosure provides a method of separating luterion, which includes the steps of:
(a) boiling of a plant or food in solvent, obtaining a condensate by cooling the vaporized luterion and filtering such condensate with a filter having pore size of 0.8 μm to 1.2 μm;
(b) centrifuging the filtered condensate; and
(c) separating the luterion from the centrifuged supernatant.

The present disclosure also provides another method of separating luterion, which includes the steps of:
(a) adding a particle with surface expression of an antibody or aptamer that uniquely binds to the suface antigens of luterion to an extract containing the luterion so as to induce binding of the particle with the luterion,; and
(b) recovering the luterion bound to the particle.

The present disclosure also provides a method of culturing the luterion, including adding water to the luterion and proliferating the same at 18° C. to 30° C. under IR light irradiation or pressurization.

The present disclosure further provides a method of culturing the luterion, including proliferating the luterion in a medium containing sugar at pH 5 to pH 9 and 18° C. to 30° C.

DETAILED DESCRIPTION OF THE EMBODIMENT

Figure 1:
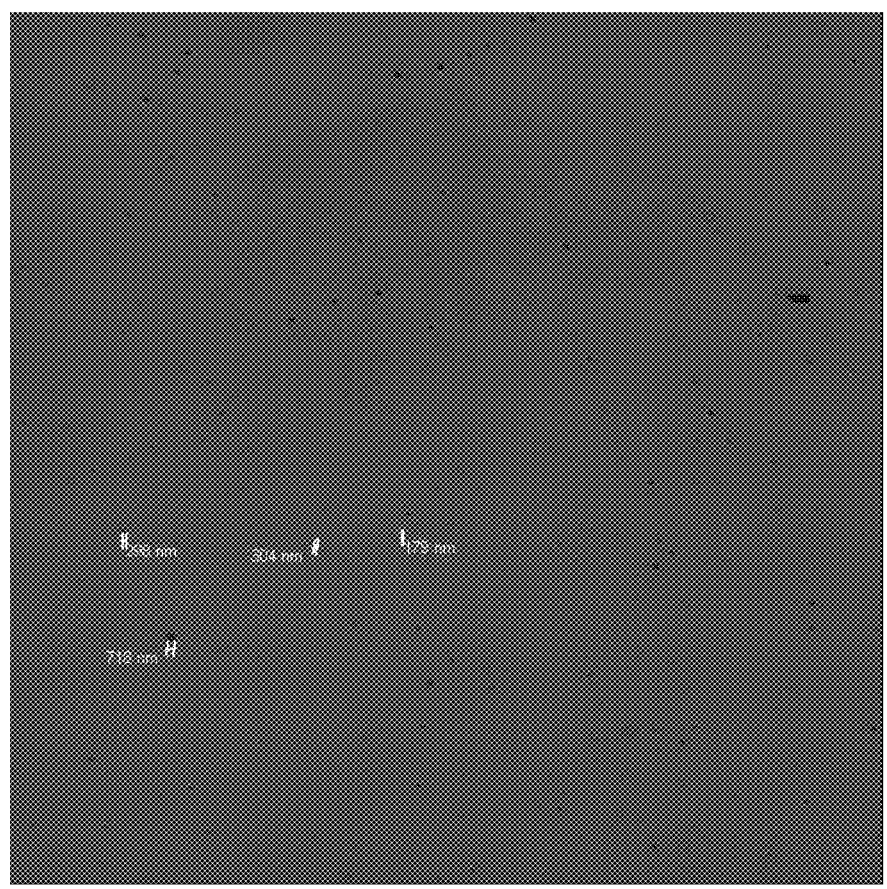
FIG. 1 is a photograph of luterion taken by a confocal laser scanning microscope (Zeiss), together with its size.
Figure 2:
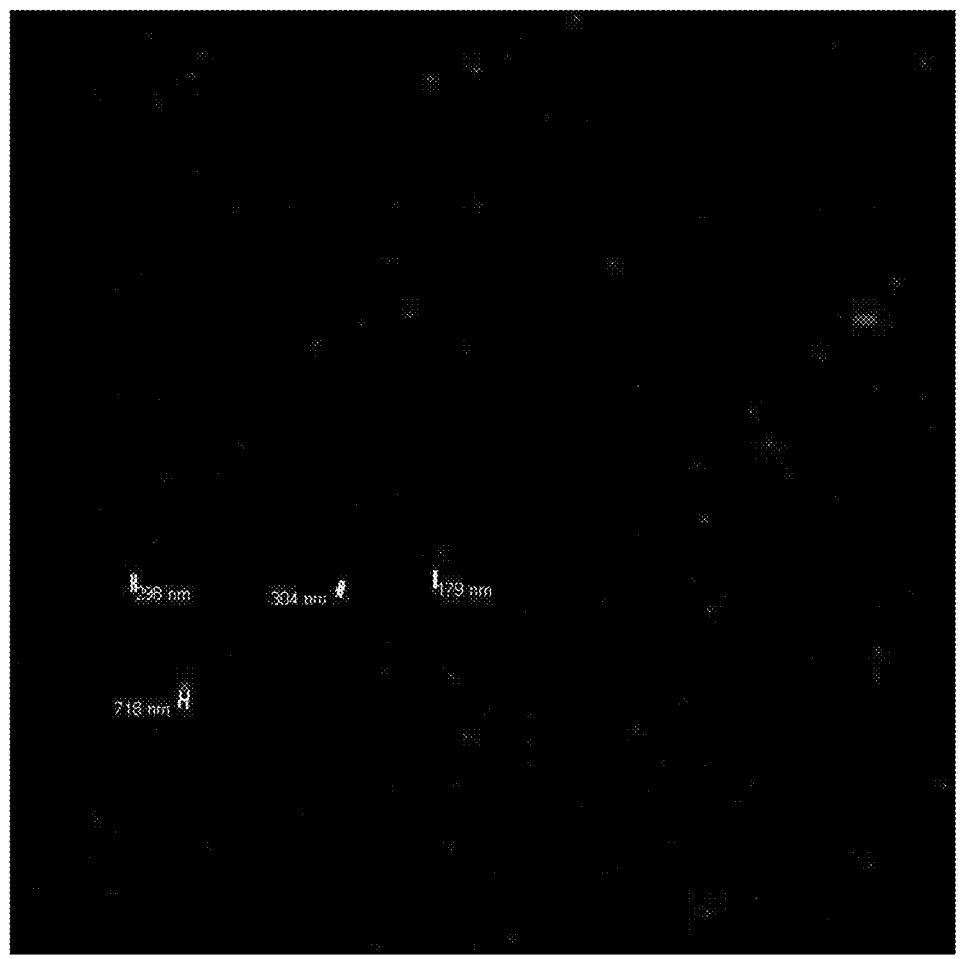
FIG. 2 is an image showing the presence or absence of staining of the luterion with Mito-tracker.
Figure 3:
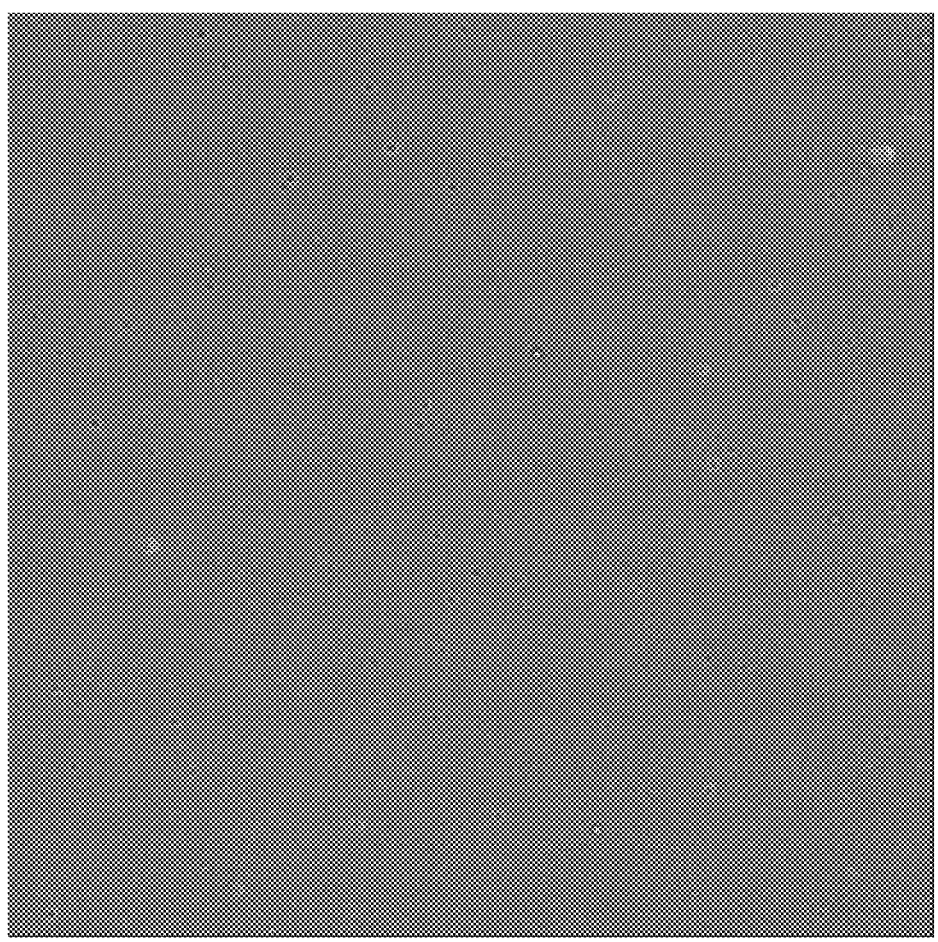
FIG. 3 is an image showing the presence or absence of staining of the luterion with Rhodamine 123.

Unless otherwise defined, all technical and scientific terms used herein have the same meaning as commonly understood by those skilled in the art to which the present disclosure belongs. In general, the nomenclature used herein and the experiment methods described below are well known and commonly used in the art.

The terms "luterial" and "luterion" as used herein is a micro material named by the present inventors, having a size of 50 nm to 400 nm and are present in all living organisms including animals and plants, and growing in a size from virus-like size up to 800 nm to 1200 nm upon fusion. These micro materials are classified as a mutant when the size is larger than 1200 nm, and they expresses a gene abnormality and pathological phenomenon at this size.

Both of the luterial and luterion are distinguished from exosome or microvesicle in that they have DNA and RNA and have motility and adhesion. It is well established that mitochondria are stained by Janus green B and fluorescent dyes such as Rhodamine 123, Mitotracker, Acridine orange, and DAPI, and the luterion and luterial are also confirmed to be stained by the same dyes (See FIGS. 1 to 6). They have a membrane structure similar to that of mitochondria and yet with an incomplete internal cristae structure. It is observed in the same laser wavelength range as the mitochondria. Thus, they may also be referred to as pseudo-mitochondria, mitochondrial analog, or proto-mitochondria.

The luterial refers to a nano-sized micro material that exists in the host's body in the ecosystem. In the case of animals including humans, it may exist in blood, saliva, lymphatic fluid, semen, vaginal fluid, breast milk (especially colostrum), cord blood, brain cells, spinal cord, or bone marrow. On the other hand, the luterion refers to a nano-sized micro material mainly in plants that the hosts may use as food.

The luterion does not dissolve or disappear in a short time at room temperature, and it is not mutated by fusion even when stored for a long time.

According to an aspect of the present disclosure, the luterion has at least one characteristic selected from the followings:

(a) a circular or oval shape with a size of 50 nm to 800 nm, having motility
(b) having a nucleic acid;
(c) showing a similar reaction as mitochondria upon immunochemical fluorescence staining;
(d) showing fusional and/or fissional physiological phenomena;
(e) maturing to a size of up to 500 nm in the absence of fusion, maturing into pseudo-mitochondria containing DNA, and showing a mitochondria-like structure on an image obtained by a scanning electron microscope (SEM) or transmission electron microscope (TEM);
(f) showing phototropism different from the exosome
(g) undergoing fission upon IR irradiation or pressurization;
(h) expressing CD332, CD133, CD73 or CD39 as a surface antigen;
(i) showing autofluorescence;
(j) producing ATP at a size of 400 nm or less;
(k) double membrane or multi membrane structure;
(l) showing adherence;
(m) inhibiting telomerase activity of cancer cells;
(n) promoting telomerase activity of normal cells;
(o) having cell permeability; and
(p) having blood-brain-barrier (BBB) permeability.

According to one exemplary embodiment of the present disclosure, the luterion is a micro material named by the present inventors, having a size ranging from virus-like to about 500 nm (normal fission stage: 50 nm to 500 nm, abnormal fusion stage: 800 nm or more). It is distinguished from micro vesicles in that it contains DNA and/or RNA, and has motility. It also has the characteristics of autofluorescence and photosynthesis. Mitochondria are identified by fluorescent staining with Rhodamine 123, Mitotracker, Acridine Orange, DAPI, and Janus green B. Since the luterion is stained by the same staining agent as that of mitochondria, it is possible to confirm whether the luterion is properly separated by fluorescent staining with the above dye (See FIGS. 1 to 6).

In addition, it can be confirmed that the luterion contains RNA as well as DNA by a DAPI and Acridine orange (AO) staining method. Specifically, it can be confirmed that RNA is stained with an acridine orange dye in orange at an excitation wavelength of 460 nm and at an emission wavelength of 650 nm. DNA is stained in green at an excitation of 502 nm and at an emission of 525 nm, and the presence of DNA in luterionn is confirmed by the DAPI staining method. It can be confirmed that the luterion of the present disclosure contains RNA and DNA using the above staining method.

Figure 8:
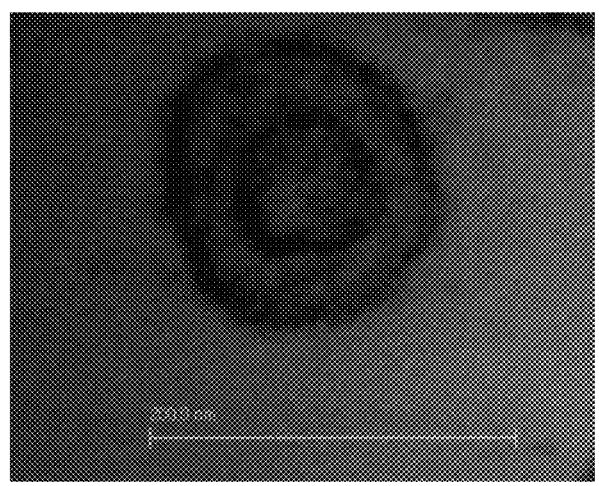
FIG. 8 is an image obtained by TEM electron microscope, showing that the luterion has a double membrane structure.
Figure 9:
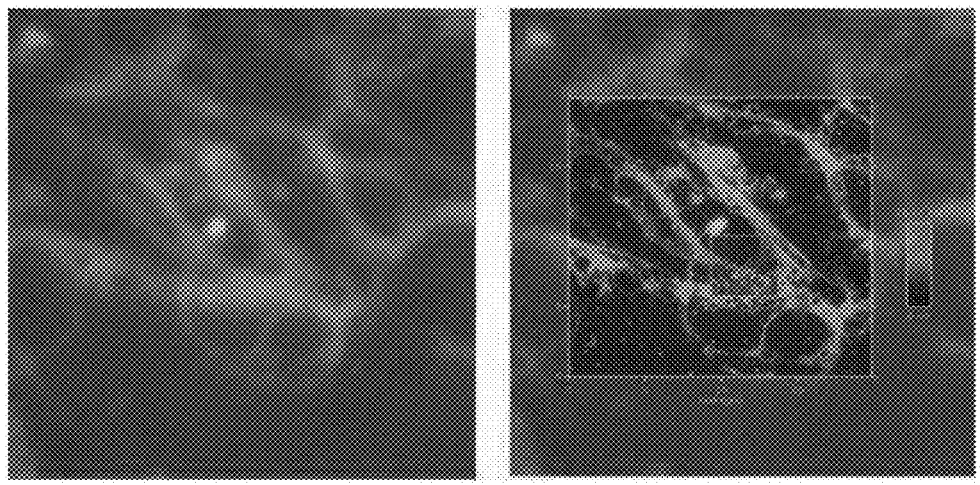
FIG. 9 is an image obtained by an atomic force microscope, showing that the luterion contains a nucleic acid therein.

In one exemplary embodiment of the present disclosure, it is confirmed that the luterion has a double membrane or a multilayer membrane (See FIG. 8), and nucleic acid, particularly RNA, is contained in the luterion (See FIGS. 9 and 10).

Conventionally, it is not known that the luterion exists in a plant or a food. Therefore, there is no description about a method of separating or culturing the luterion. According to the present disclosure, it is possible to provide a method for effectively isolating and culturing the luterion.

In another aspect, the present disclosure relates to a method for isolating the luterion comprising the steps of: (a) filtering the condensate obtained by cooling the water vapor or gas obtained from boiling the plant or food in a solvent, with a filter having a pore size of 0.8 μm to 1.2 μm; (b) centrifuging the filtered condensate; and (c) separating the luterion from the centrifuged supernatant.

First, the step (a) is a step of filtering the condensate obtained by cooling the vapor or gas obtained from boiling a plant or food, using a filter having a pore size of 0.8 μm to 1.2 μm.

In one exemplary embodiment, the above extraction by boiling can be carried out by adding a solvent to a plant or food and boiling while bubbling intermittently using a gas at the temperature between 50° C. and 90° C. The luterion used in the present disclosure has a density of 1 or less, and the density is less than that of protein, and thus can be separated from a plant or a food by a steam distillation method, but is not limited thereto.

When the luterion is boiled while bubbling intermittently using a gas at 50° C. to 90° C., the luterion is isolated in the form of water vapor with gas. When boiling it with bubbling, the boiling point of the plant or food solution containing the luterion may be lowered to prevent decomposition, deterioration, or damage of the luterion.

In some cases, the step (a) can be carried out by boiling for 8 to 10 hours and bubbling for 20 minutes to 30 minutes every 2 to 3 hours to prevent the luterion of the plant or food from entangling, so as to increase efficiency of isolating the luterion.

Figure 37:
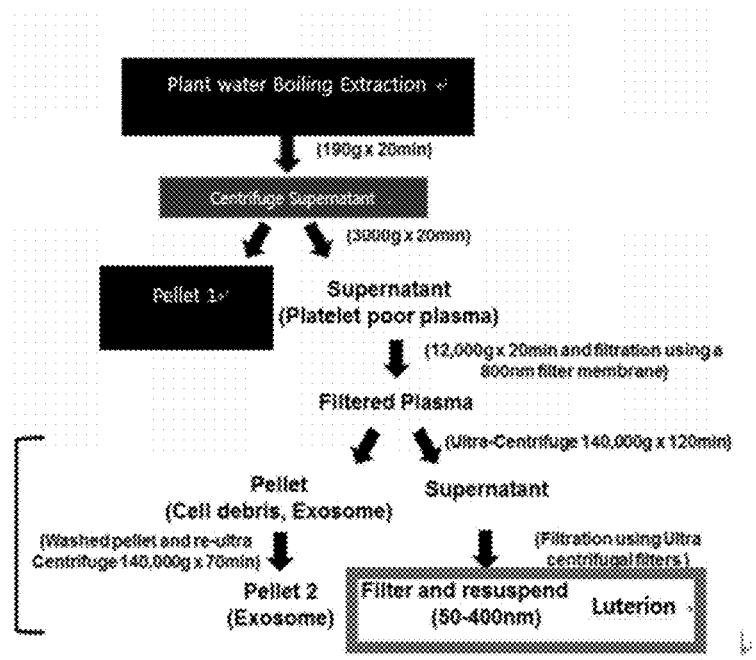
FIG. 37 is a schematic diagram specifically showing an extraction step of the luterion.

The details of the extraction-filtering in the step (a) are shown in FIG. 37. A solvent such as distilled water is added to the plant or food, and the extraction is obtained through boiling, and then subjected to primary centrifugation at about 100 g to 250 g, preferably 190 g, and then spun down to remove impurities, and subjected to secondary centrifugation about 1000 g to 5000 g, preferably about 3000 g. The supernatant can be collected after stabilizatioin for several minutes (preferably about two hours). In some cases, at this time, luterion can be stained with anti-CD332 tagged with a fluorescence marker and checked for its motility for the initial confirmation of the presence of the luterion. Thereafter, in order to obtain pure luterion, a third centrifugation can be carried out at 100,000 g to 150,000 g, preferably 120,000 g.

Thereafter, the filtrate using a filter of about 800 nm is collected, and debris pellet such as exosome or internal plant such as plasma is removed. Thereafter, the supernatant containing no pellet can be collected by further centrifugation at 140,000 g or more. The supernatant is filtered with a 400 nm filter, the filtrate is collected, and then the CD332 of the luterion is stained again to confirm its motility. In addition, the luterion can be collected by filtering with a 50 nm filter, collecting the unfiltered part on the filter to obtain the luterion, and fixed at a pH of 1 or a temperature of −90° C. or less.

In one exemplary embodiment, the plant may be selected from the medicinal plants listed in Tables 1 to 4. Since the luterion is present in all plants, the luterion is not limited to the medicinal plants described in Tables 1 to 4.

TABLE 1

| Group | Name of Herb | Scientific Name |
|---|---|---|
| A | Ganghwal | *Ostericum koreanum* Maximowicz |
| | Dokhwal | *Aralia continentalis* Kitagawa |
| | Hyeonggae | *Schizonepeta tenuifolia* Briquet |
| | Bangpung | *Saposhnikovia divaricata* Schischkin |
| | Saengjihwang | *Rehmannia glutinosa* Liboschitz ex Steudel |
| | bongnyeong | *Poria cocos* Wolf |
| | Jeonho | *Angelica decursiva* Franchet et Savatier |
| | Chajeonja (jilkyungee) | *Plantago asiatica* Linne |
| | Jigolpi (gugija) | *Lycium chinense* Miller |
| | Siho | *Bupleurum falcatum* Linne |
| | Taeksa | *Alisma orientale* Juzepzuk |
| | Moktong | *Akebia quinata* Decaisne |
| | Hyeonsam | *Scrophularia ningpoensis* Hemsley |
| | Gwalluin | *Trichosanthes kirilowii* Maximowicz |
| | Jeoryeong | *Polyporus umbellatus* Fries |
| | Hwangnyeon | *Coptis japonica* Makino |
| | Gosam | *Sophora flavescens* Solander ex Aiton |
| | Hwangbaek | *Phellodendron amurense* Ruprecht |
| | Jimo | *Anemarrhena asphodeloides* Bunge |
| | Sukjihwang | *Rehmannia glutinosa* Liboschitz ex Steudel |
| | Sansuyu | *Cornus officinalis* Siebold et Zuccarini |
| | Mokdanpi | *Paeonia suffruticosa* Andrews |
| | Bokbunja | *Rubus coreanus* Miquel |
| | Indongdeung | *Lonicera japonica* Thunberg |
| | Bakha | *Mentha arvensis* Linne var. piperascens Malinvaud ex Holmes |
| | Chija | *Gardenia jasminoides* Ellis |
| | Yeongyo | *Forsythia viridissima* Lindley |
| | Ubangja | *Arctium lappa* Linne |

TABLE 2

| Group | Name of Herb | Scientific Name |
|---|---|---|
| C | MihuDeung (Darae) | *Actinidia arguta* PLANCH |
| | Mihudo | *Actinidia arguta* Fructus |
| | mokgwa | *Chaenomelis* Fructus |
| | Podogeun | *Vitis vinifera* Radix |
| | Nogeun | *Phragmitis* Rhizoma |
| | Aengdo | *Prunus tomentosa* Thunb |
| | Ogapi | *Acanthopanax sessiliflorum* SEEM |
| | Songhwabun | *Pinus densiflora* S. et Z |

TABLE 2-continued

| Group | Name of Herb | Scientific Name |
|---|---|---|
| | Jeodugangbansi | rice bran on a mallet head |
| | Cheongsongjeol | *Pinus tabulaeformis* |
| | Gyomaekmi | *Semen Fagopyri* |

TABLE 3

| Group | Name of Herb | Scientific Name |
|---|---|---|
| U | Sumac | *Rhus verniciflua* |
| | Cheongung | *Cnidium officinale* Makino |
| | Danggwi | *Angelica Gigas* Nakai |
| | Jinpi | *Citri Unshius* Pericarpium |
| | Jeokhasuo | *Polygonum multiflorum* Thunberg |
| | Baeksuo | *Cynanchum wilfordii* Hemsley |
| | Ginseng | *Panax ginseng* C. A. Meyer |
| | Baekchul | *Atractylodes japonica* Koidzumi |
| | Changchul | *Atractylodes lancea* De Candlle |
| | Geongang (ginger) | *Zingiber officinale* Roscoe |
| | Yukgye (cinnamon) | *Cinnamomum cassia* Presl |
| | Cheongpi (mandarin tree) | *Citrus unshiu* Markovich |
| | Gwakhyang | *Agastache rugosa* O. Kuntze |
| | Jasoyeop | *Perilla frutescens* Britton var. *acuta* Kudo |
| | jujube | *Zizyphus jujuba* Miller var. *inermis* Rehder |
| | Gamcho | *Glycyrrhiza uralensis* Fischer |
| | Buja | *Aconitum carmichaeli* Debeaux |
| | Hyangbuja | *Cyperus rotundus* Linne |
| | Hwanggi | *Astragalus membranaceus* Bunge |
| | Baekjagyak | *Paeonia lactiflora* Pallas |
| | Sohoehyang | *Foeniculum vulgare* Miller |
| | Goryanggang | *Alpinia officinarum* Hance |
| | Daebokpi | *Areca catechu* Linne |
| | Banha | *Pinellia ternata* Breitenbach |
| | Namseong | *Arisaema amurense* Maximowicz var. *serratum* Nakai |
| | Ikji | *Alpinia oxyphylla* Miquel |
| | Jisil (trifoliate orange) | *Poncirus trifoliata* Rafinesque |
| | Hubak | *Magnolia ovobata* Thunberg |
| | Mokhyang | *Aucklandia lappa* Decne |
| | Osuyu | *Evodiae rutaecarpa* Bentham |
| | Pagoji | *Psoralea corylifolia* Linn |
| | Chongbaek(Root of green onion) | *Allium fistulosum* Linn |
| | Sain | *Amomum villosum* Loureiro |
| | Sansa | *Crataegus pinnatifida* Bunge |

TABLE 4

| Group | Name of Herb | Scientific Name |
|---|---|---|
| G | Mahwang | *Ephedra sinica* Staph |
| | Gamguk | *chrysanthemum indicum* Linne |
| | Gilgyeong (balloon flower) | *Platycodon* grandiflorum |
| | Haengin (apricot tree) | *Prunus armeniaca* var. ansu Max. |
| | Baekji | *Angelica dahurica* BENTH. et HOOK |
| | Maengmundong | *Liriope muscari* BALL |
| | Cheonmundong | *Asparagus cochinchinensis* Merr |
| | Sanyak (Chinese Yam) | *Dioscorea japonica* THUNB |
| | Sanjoin | *Zizyphus jujube* |
| | Yongannyuk | *Dimocarpus longan* Lour |
| | Wonji | *Polygala tenuifolia* |
| | Seokchangpo | *Acorus graminens* SOLAND |
| | Omija | *Schizandra chinensis* BAALL |
| | Geonyul | *Castanea crenata* S. et Z. |
| | Uiiin | *Coix lachryma-jobi* var. ma-yuen |

TABLE 4-continued

| Group | Name of Herb | Scientific Name |
|---|---|---|
| | Nabokja (daikon) | Raphanus sativus L |
| | Galgeun (kudzu) | Pueraria thunbergiana |
| | Hwanggeum | Scutellaria baicalensis GEORG |
| | Gobon | Angelica tenuissima NAKAI |
| | Nogyong | Cervi Parvum Cornu |
| | Daehwang | Rheum palmatum |
| | Seungma | Cimicifuga heracleifolia KOM |
| | Baekjain | Biota orientalis ENDL |
| | Sangbaekpi (mulberry) | Morus alba L |
| | Gwandonghwa | Tussilago farfara |
| | Baekgwa | Gingko biloba L |
| | Sahyangpul | Thymus vulgaris |
| | Jogak | Gleditsia japonica Miquel var. koraiensis Nakai |

Further, it is expected that the luterion contained in the plant is distributed in a large amount on the stem part of the plant, and it is preferable to separate the luterion from the plant containing the stem portion.

The above condensed liquid can be obtained by collecting water vapor or gas vaporized by the boiling, and then cooling it. It is possible to obtain the luterion in a state separated from the collected vaporized water vapor or gas or to obtain the luterion in a mixed state therewith. When the luterion is in a mixture state with the vaporized water vapor or the gas, the luterion can be obtained through a further separation process.

In some cases, the step of irradiating the condensate obtained in the step (a) with an IR ray may be added for separation of the luterion. For example, it is possible to collect highly concentrated luterion by irradiating the condensate with the IR light for 20 minutes to 60 minutes, preferably 30 minutes to 40 minutes to prevent the deformation of luterion, and collecting the luterion moving toward the light.

The step (b) is a step of filtering the obtained condensate using a filter having a pore size of 0.8 μm to 1.2 μm. A filter having a pore size of 0.8 μm to 1.2 μm is an optimum size selected by the inventors of the present disclosure in consideration of the long diameter of the luterion. Following the filtration, the desired luterion can be isolated from the condensate obtained in the step (a).

The step (b) is a step of centrifuging the filtered condensate. A higher purity luterion can be obtained through this step. The centrifugation may be repeatedly performed at 1200 g to 5000 g for 5 to 10 minutes, but centrifugation condition can be adjusted for improving the purity of the luterion.

The step (c) is a step of separating the luterion from the centrifuged supernatant fractioni. For example, the centrifuged supernatant is irradiated with IR light having a wavelength of 200 μm to 600 μm to gather the luterion moving toward the light. Also the luterion can be further separated from the centrifuged supernatant by collecting the luterion that expresses the surface antigens such as CD332, CD133, CD73 and CD39. But it is not limited thereto.

After the separation step (c), the luterion may be further separted using a filter having the pore size of less than 50 nm, and then collecting the unfiltered substance trapped on the filter. Through the above process, micro materials other than the luterion can be removed, and the luterion having a size of 50 nm or more can be obtained.

Figure 27:
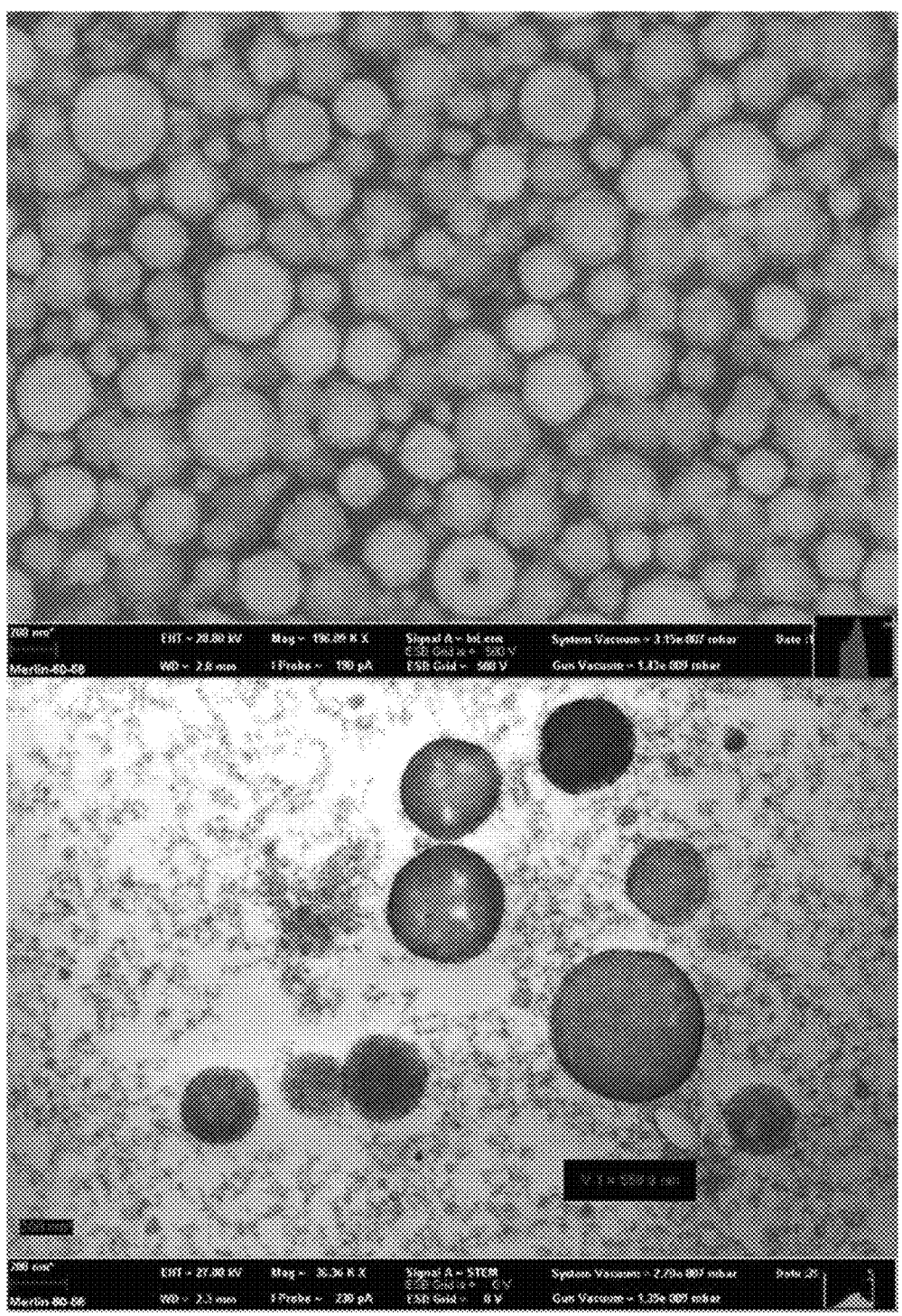
FIG. 27 shows the image of the luterion obtained from a scanning electron microscope (SEM) of Carl Zeiss.
Figure 28:
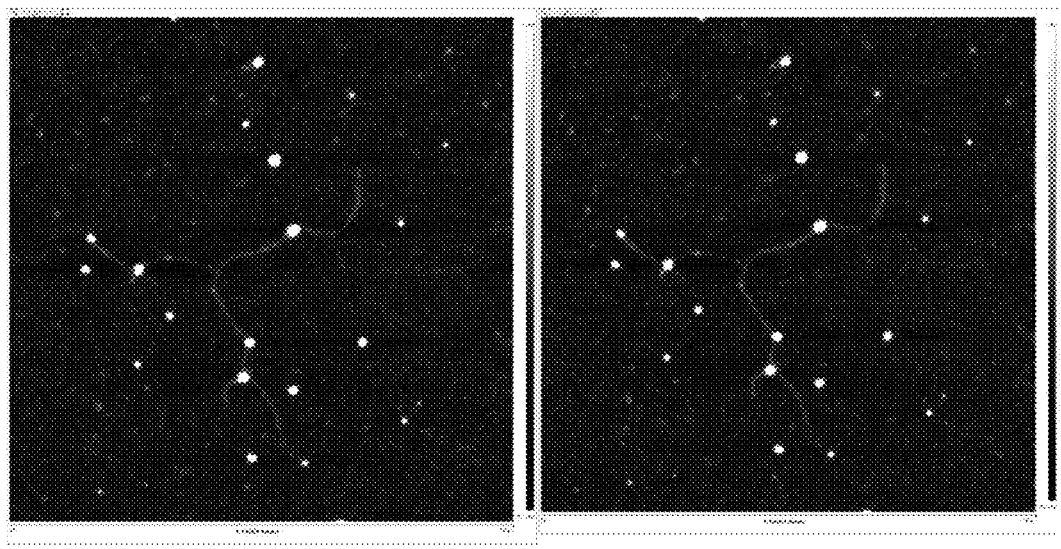
FIG. 28 shows the an image of the luterion obtained from a Bruker Fast Scan AFM atomic force microscope.
Figure 29:
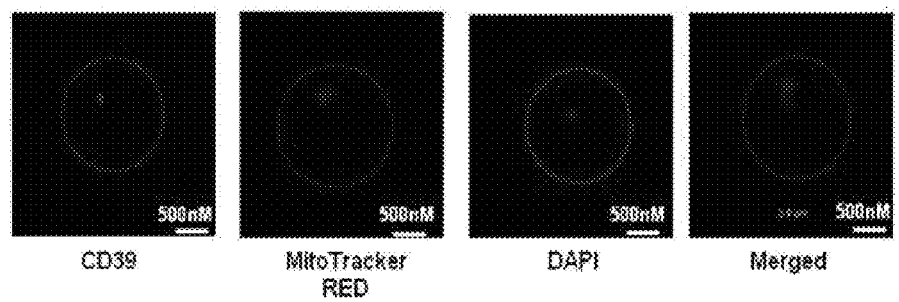
FIG. 29 shows the costaing pattern of the luterion after adding a fluorescently labelled anti-CD39 antibody, Mito-tracker and DAPI, each or combination thereof.
Figure 30:
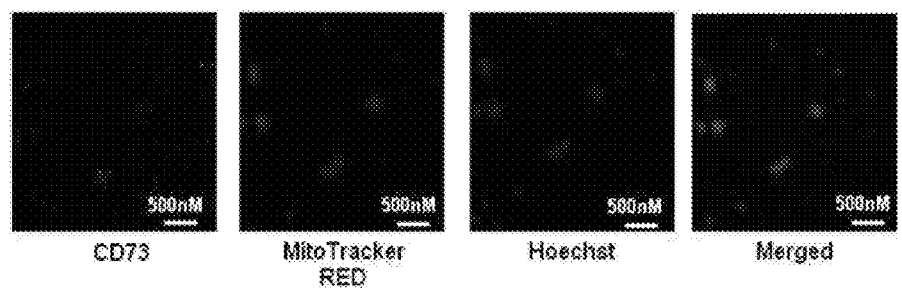
FIG. 30 shows the costaing pattern of the luterion after adding a fluorescently labelled anti-CD73 antibody, Mito-tracker and Hoechst, each or combination thereof.
Figure 31:
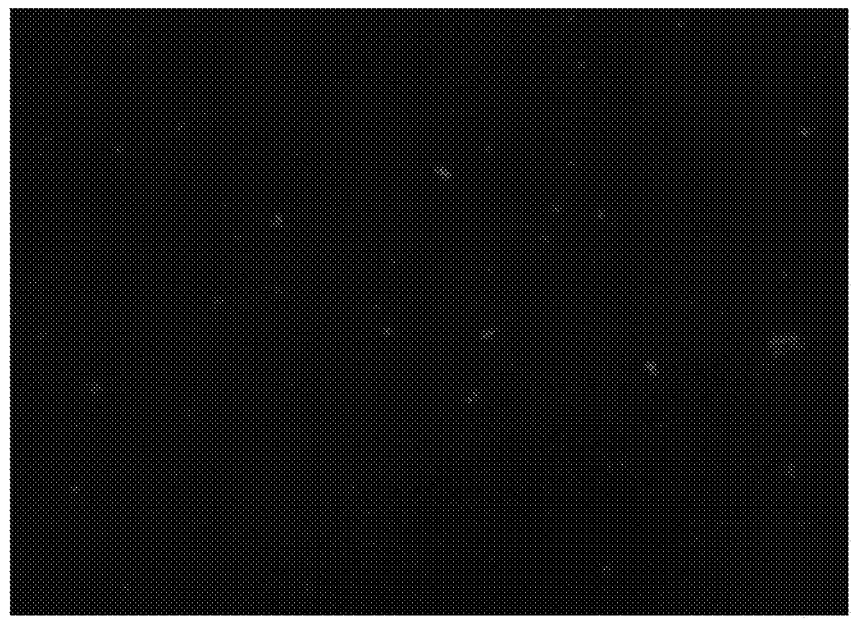
FIG. 31 shows the results of binding luterion with fluorescently labelled anti-CD332 antibody.
Figure 32:
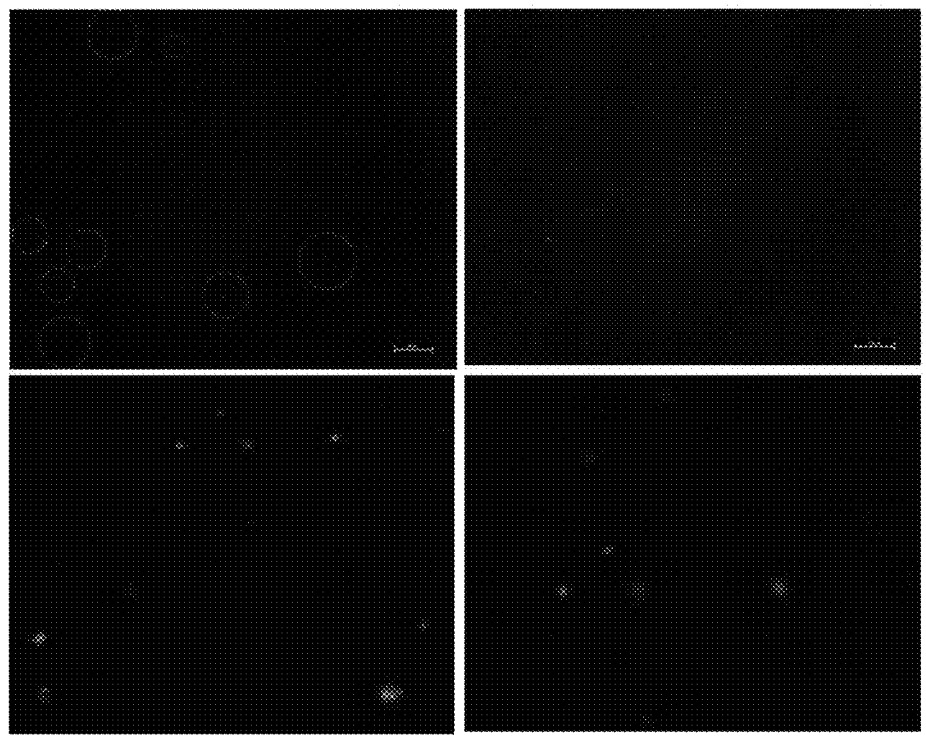
FIG. 32 shows the result of binding luterion with fluorescently labelled anti-CD133 antibody, and the upper part thereof shows the result of anti-CD133-PE (Phycoerythrin) fluorescence staining and the lower part thereof shows the result of anti-CD133-FITC fluorescence staining.

In some cases, they can be classified as the luterion of 50 nm to 200 nm, 200 nm to 400 nm, 400 nm to 600 nm, 600 nm to 800 nm, and 800 nm to 1000 nm in size, respectively, sequentially using the filters of 200 nm, 400 nm, 600 nm, 800 nm, and 1000 nm. The luterion according to the present disclosure can be observed through a dark-field microscope or a confocal microscope, and it is possible to classify as the luterion of 50 nm to 200 nm (generating stage), 200 nm to 400 nm (maturing stage), 400 nm to 600 nm (splitting stage), and 600 nm to 800 nm (oversplitting stage) by sequencially filtering the luterion through the filters of 800 nm, 600 nm, 400 nm and 800 nm. (See FIGS. 27 and 28).

Thereafter, the step of fixing the luterion at specific pH and temperature conditions may be further added. For example, it can be fixed at pH 7 or lower and 0° C. or lower. Preferably, it can be fixed at pH 1 to 5 and at −90° C. to 0° C. In one exemplary embodiment of the present disclosure, it is confirmed that the fixation of the motile luterion is possible under a temperature of 0° C. or less and pH of 1 to 3 conditions. Fixing the luterion can improve the separation efficiency.

It may also include an additional proliferation step, for example a fission inducing step. Fission can be induced by applying a pressure of 25,000 psi (pounds per square inch) or more. In one exemplary embodiment of the present disclosure, it is confirmed that a pressure of 25,000 psi to 35,000 psi is applied to induce the fission. At this time, temperature is maintained at 10° C. to 20° C., and the pH 1 to 3 conditions used for fixing are maintained.

In another aspect, the present disclosure relates to a method of isolating the luterion, comprising the steps of: (a) adding a particle to an extract comprising the luterion so as to induce combination of the particle and the luterion, the particle having a fixed antibody or aptamer therein, which specifically binds to the luterion surface antigen; and (b) recovering the luterion bound to the particle.

In the present disclosure, in order to efficiently isolate a large amount of the luterion based on the expression of a specific antigen on the surface of the luterion, separation of the luterion is attempted using an antibody or an aptamer-fixed particle against the specific antigen. As a result, in one exemplary embodiment of the present disclosure, it is confirmed that the luterion can be separated in a large amount in a shorter time than conventional methods.

The extract containing the luterion may be, for example, (i) a hot water extract of a plant or food, (ii) a solvent extract of the plant or food, or (iii) a condensate of gas generated by heating the plant or food in the presence of the solvent.

The hot-water extract is not particularly limited as long as the physiologically active substance is extracted from plants using water having a temperature of, for example, 40° C. or higher. When hot water extraction is used, the problem caused by the toxicity of the organic solvent does not occur. The solvent extract may be extracted using a solvent, for example, ether, methanol, ethanol, and hexane.

The condensate is prepared by adding distilled water to a plant or a food, boiling it while bubbling it intermittently using a gas at 50° C. to 90° C., and collecting water vapor or gas vaporized by the boiling, and cooling the same.

"Luterion surface antigen" according to the present disclosure is attached to the cell surface membrane through a carboxyl terminal domain containing a hydrophobic amino acid lying on the lipid layer of the luterion membrane and can exert a biological antigen effect, and may include, for example, CD39 (Ectoucleoside triphosphate diphosphohydrolase 1; ENTPD1), CD73 (Ecto-5' nucleotidase; NT5E), HBsAg, SLC3A2, CD109, LY9, CD332, CD133, or CD53, preferably CD332, CD133, CD39, or CD73.

The "antibody" means a protein molecule that is specifically bound and directed against an antigenic site. In the present disclosure, particles are fixed to a substance capable of specifically binding to a luterion surface antigen. An antibody that specifically binds to the antigen can be used. Antibody that may be used in the present disclosure may be, for example, an anti-CD332 antibody, anti-CD133 antibody, anti-CD39 antibody, or anti-CD73 antibody. An antibody that is commercially available can be used. An aptamer that binds to the surface-expressing antigen may be used instead of this antibody.

The "particle" may have magnetic, luminescent, electrostatic, and ionic properties depending on their properties and may have micro or nano sizes depending on their size. If the luterion may be separated through binding with antibodies, but it is not limited to, it can be selected from, for example, a magnetic particle, silica particle, quantum dot particle, glass particle, polymer particle, fiber particle, and fluorescent particle. The particle may include a particle having magnetic properties and fluorescence properties at the same time, magnetic particles bound by quantum dots and gold and silver particles.

The particle may be, for example, a magnetic particle, and this magnetic particle is magnetic and moves by a magnetic field. The magnetism may be paramagnetic. The magnetic particle may include, for example, a metal material, a magnetic material, or a magnetic alloy. The magnetic particle may be a particle that expresses magnetism, but the magnetic particle is not limited thereto in the present disclosure. It may be a magnetic particle which is not magnetized themselves, but may be a metal particle capable of having magnetism or attracted to magnetic force. The metal particle may be made of any one selected from the group consisting of, for example, oxides of iron, aluminum, cobalt, nickel, manganese, tin, zinc, cadmium, magnesium, copper, barium, lithium, or yttrium. Of these, iron is preferably selected. The particle is ferromagnetic in micrometer size, while the small particle in nanometer size is hypermagnetized. Such particle is easy to be synthesized and its size can be easily adjusted. For example, the particle may have a size of 1 nm to 1,000 nm, preferably 10 nm to 1,000 nm, more preferably 10 nm to 500 nm, and most preferably 10 nm to 100 nm.

In some cases, the magnetic particle may be modified to maintain dispersibility and safety in the magnetic particle. For example, carbon may be coated to modify the magnetic particle.

It may further include functional groups suitable for binding to antibody or aptamer. The functional group may be, for example, an amide group, an ester group, an amine group, a carboxyl group, a thiol group (SH), an epoxy group, a phenyl group, a sulfone group, an alkoxy group, an aldehyde group, and a ketone group. The amine group ($NH_2$) may be monoamine, diamine, triamine, ethylene diamine, or diethylenetriamine.

In the step of recovering the luterion bound to the particle, when the particle is a magnetic particle, the step (b) may particularly involve a recovery of the luterion bound to the magnetic nanoparticle using the externally applied magnetism.

After such recovery of the magnetic nanoparticle bound with the luterion via interaction between the luterion and the particle coated with the luterion-specific antibodies or aptamers, luterion may be pelleted using a magnet or a magnetic activated cell sorter (MACS) at room temperature, followed by the removal of the supernatant and resuspension of the pellet in the buffer solution, and sequential passage through an agglutination film and filtration membranes to captrue the luterion-antibody-magnetic particle composites.

In the present disclosure, the step (b) may also particularly involve recovering of the fluorescent particles bound with the luterion using a fluorescence-activated cell sorter.

The recovery using the fluorescence-activated cell sorter is a process of classifying the micro-materials according to the type and intensity of their fluorescence for qualitative and quantitative analysis. It involves the "fluidic system" that enables the fluorescent particles to flow through a predetermined tube, an "optical system" for observing the micro-materials flowing under the control of the fluidic system, and an "electronic system" converting the optical signal of the optical system into an electric signal.

The fluorescence activated cell sorting device is a device that efficiently classifies and collects various cells according to their specific fluorescent properties and is widely used in life sciences (e.g., animal science, botany, microbiology, agriculture, fisheries science, and forestry) and medical research. The fluorescent substance contained in the fluorescent particles of the present disclosure may be any fluorescent substance that can be used for living body imaging. The fluorescent substance includes, but is not limited to, one selected from the group consisting of rhodamine and its derivatives, fluorescein and its derivatives, coumarin and its derivatives, acridine and its derivatives, pyrene and its derivatives, erythrosine and its derivatives, eosin and its derivatives, 4-acetamido-4'-isothiocyanatostilbene-2,2'disulfonic acid. A more specific example of the fluorescent substance is as follows:

Rhodamine and its derivatives: 6-carboxy-X-rhodamine (ROX), 6-carboxyrhodamine (R6G), Lissamine rhodamine B sulfonyl chloride, rhodamine (Rhod), rhodamine B, rhodamine 123, rhodamine X isothiocyanate, sulforhodamine B, sulforhodamine 101, sulfonyl chloride derivatives of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, terbium chelate derivatives, Alexa derivatives, Alexa-350, Alexa-488, Alexa-547, and Alexa-647; fluorescein and its derivatives: 5-carboxyfluorescein (FAM), 5-(4, 6-dichlorotriazin-2-yl)aminofluorescein (DTAF), 2'7'-dimethoxy-4'5'-dichloro-6-carboxyfluorescein (JOE), fluorescein, fluorescein isothiocyanate, QFITC (XRITC), fluorescamine, IR144, IR1446, malachite green isothiocyanate, 4-methylumbelliferone, ortho-cresolphthalein, nitrotyrosine, pararosaniline, phenol red, B-phycoerythrin, and o-phthaldialdehyde; coumarin and its derivatives: coumarin, 7-amino-4-methylcoumarin (AMC, coumarin 120), 7-amino-4-trifluoromethylcoumarin (coumarin 151), cyanocin, 4'-6-diaminidino-2-phenylindole (DAPI), 5',5''-dibromopyrogallol-sulfonephthalein (Bromopyro-gallol Red), 7-diethylamino-3-(4'-isothiocyanatophenyl)-4-methylcoumarin diethylenetriamine pentacetate, 4-(4'-diisothiocyanatodihydro-stilbene-2,2'-disulfonic acid, 4,4'-diisothiocyanatostilbene-2,2'-disulfonic acid, 5-[dimethylamino] naphthalene-1-sulfonyl chloride (DNS, dansyl chloride), 4-(4'-dimethylaminophenylazo)benzoic acid (DABCYL), and 4-dimethylaminophenylazophenyl-4'-isothiocyanate (DABITC); acridine and its derivatives: acridine, acridine isothiocyanate, 5-(2'-aminoethyl)aminonaphthalene-1-sulfonic acid (EDANS), 4-amino-N-[3-vinylsulfonyl)phenyl] naphthalimide-3,5disulfonate (LuciferYellow VS), N-(4-anilino-1-naphthyl)maleimide, anthranilamide, and Brilliant Yellow; pyrene and its derivatives: pyrene, pyrene butyrate, succinimidyl 1-pyrene butyrate, and Reactive Red 4 (Cibacron Brilliant Red 3B-A); erythrosine and its derivatives: erythrosine B, erythrosine isothiocyanate, and ethidium;

eosin and its derivatives: eosin, and eosin isothiocyanate; and 4-acetamido-4'-isothiocyanatostilbene-2,2'disulfonic acid.

In the present disclosure, when the particles are electrostatically charged particles, the step (b) may include forming a dipole moment on the particles by applying a non-uniform electric field, and recovering the ionic particles bound to the luterion by electrostatic attraction.

A method of forming a dipole moment on particles by applying the non-uniform electric field and recovering an ionic particle bound with the luterion by an electrostatic attraction can be performed using an electric particle classifier (different mobility analyzer, DMA), which is a type of particle separating apparatus. The electric particle classifier is a device for classifying particles using the difference in the mobility of the particle due to electrostatic force, and is also called a differential electric mobility analyzer or a differential particle electrostatic classifier. Specifically, the electric particle classifier is a device for sorting mono-disperse particles having a desired diameter from the poly-disperse particles based on the theory that the moving speed of the charged particle is a function of the particle diameter.

In the present disclosure, when the particle is an ionic particle, for example, an anionic or cationic particle, the step (b) may involved the recovery of the ionic particle bound to the luterion using the electrostatic attraction.

The method of recovering the fiber particle bound with the luterion by the electrostatic attraction can be performed through the electric particle classifier (different mobility analyzer, DMA).

The present disclosure may further include retrieving the luterion from the luterion bound to the particles.

BSA/PBS buffer solution is added to the luterion bound to the particles, incubated at 25° C., and only the particle that adsorbed BSA (Bovine Serum Albumin) is separated using magnetic or ionic force, and the particle that adsorbed BSA may be further incubated with PBS to desorb the particle, isolating only the luterion.

In another aspect, the present disclosure relates to a method for culturing the luterion, comprising adding liquid to the luterion and proliferating at 18° C. to 30° C. under IR light irradiation or under pressure.

In one exemplary embodiment, the liquid added during the culture may be, but is not limited to, saline solution or PBS solution.

In another aspect, the present disclosure relates to a method for culturing the luterion, comprising proliferating the luterion in a sugar-containing medium at pH 5-9 (pH 1-3 when fixed) and at 18° C. to 30° C.

In one exemplary embodiment, the sugar may be rhamnose, glucose, galactose, fructose or xylose, and preferably glucose. In one exemplary embodiment of the present disclosure, it is confirmed that the luterion may be cultured in an optimal condition where glucose is added to DMEM or blood medium, at a concentration of about 1% to 10%, preferably 2% to 8%, at a pH of 7 and at a temperature of about 20° C. The number of cultured luterion is confirmed by counting the number of the luterion expressing luterion-specific surface antigens CD332, CD133, CD73, or CD39 and the luterion stained with mitotracker red.

The size of the luterion before culturing may be 50 nm to 200 nm, but the size thereof may be 300 nm to 500 nm after culturing according to the culturing method of the present disclosure. At this time, it is possible to keep the size of the luterion not to exceed 500 nm while observing it with a microscope. When the culture is finished, it can be classified according to size and cooled at −80° C. to be stored, stored in charged nitrogen, or stored at above 0° C., and the preservative may be added during storage.

The cultured luterion can be stored in a desired size (500 nm or less) without changing its characteristics for a certain period of time, and thus can be effectively used for the treatment of diseases using the luterion.

Specifically, the luterion according to the present disclosure can be introduced into intracellular cytoplasm. The luterion stained with red fluorescence is introduced into the cell, which confirmed that the luterion is introduced into the intracellular cytosol surroundging the nucleus stained with DAPI.

Further, as a result of the fluorescent staining of the luterion according to the present disclosure and its introduction into mice via intraperitoneal injection (IP) and oral gavage administration, it is confirmed that it passes BBB within at least 3 hours after oral administration or 5 minutes after intraperitoneal injection. By utilizing these characteristics, the luterion according to the present disclosure can overcome the limitations of drugs that could not be used as therapeutic agent due to its impermeability through the blood-brain barrier, e.g., in the treatment of degenerative brain diseases. Using this bbb-permeable properties, the luterion can be used as a therapeutic agent for degenerative brain diseases, or as a drug carrier for allowing a known drug to pass through the blood-brain barrier.

Further, the luterion according to the present disclosure has an anticancer effect that inhibits telomerase activity in cancer cells, has no effect in normal cells, or promotes telomerase activity, so as to effectively inhibit only proliferation of cancer cells.

Meanwhile, it is confirmed that the expression of telomerase is increased in normal cells by luterion treatment, thus increasing the length of telomere, which suggest that the luterion exhibits anti-aging activity by promoting telomerase activity in normal cells.

The "normal cell" means a cell that has a normal aging process, which is not a cell having the increased telomerase activity and a phenotype undergoing unlimited proliferation such as a cancer cell.

"Telomerase" means a ribonucleic acid protein that catalyzes the addition of telomeric repeats to the end of the telomere. It is believed that the telomere is a long stretch of repeating sequences covering an end of a chromosome and stabilizes the chromosome. In humans, telomeres are typically 7 kb to 10 kb in length and contain multiple repeats of the sequence -TTAGGG-. Telomerase is not expressed in most adult cells, and a length of the telomere is reduced by the continuous replication of original one. When cell replication reaches a certain number of times or more, the telomere gradually shrinks, causing the cells to enter the terminal collapse stage, which causes the cells to age. Telomerase is inactive in somatic cells, but is active in 90% of cancer cells, and telomerase inhibitors may be useful in fighting a cancer.

Furthermore, it is confirmed that the treatment of normal human fibroblasts with the luterion results in an increase in telomerase expression of the human normal cells and an increase in ATP production. In other words, it is confirmed that the luterion can suppress aging by increasing telomerase activity of normal cells. Thus, the luterion according to the present disclosure can be used in the treatment of diseases or conditions susceptible to increased telomerase expression and/or telomerase activity and is administered to patients in need of treatment so as to increase the telomerase activity in tissues or cells of the patient.

"Diseases or illnesses associated with aging" refers to development of tumors, malignant development of a cancer, myocardial infarction (heart attack), cerebellar infarction, stroke, Parkinson's disease, heart failure, atherosclerosis, hypertension, cataract, decreased visual acuity accompanying aging, muscular dystrophy, osteoarthritis, osteoporosis, bone marrow loss, multiple sclerosis, Sjogren's syndrome, rheumatoid arthritis, impaired immune function, diabetes, idiopathic pulmonary fibrosis, neurodegenerative diseases, Alzheimer's disease, Huntington's disease, and disorders resulted from, e.g., testosterone, estrogen, growth hormone, IGF-I, or reduced energy production.

"Anti-aging effect" refers to phenotype including increase in mitochondrial biogenesis and function, reduced ROS levels, prolonged lifespan of cell after division of somatic cells such as senescent and neuronal cells, prevention of the phenomenon associated with aging such as an tumorigenesis, malignant development of a cancer, cerebellar infarction, and myocardial infarction.

The mitochondria, the cell's power plant, is the most active respiratory oxygen consuming place where all cells carry out their metabolic activities. Mitochondrial functions provide the energy needed for all the activities of the cell (Boveris A et al., *Biochem. J.* 134: 707-716, 2973). Reactive oxygen species (ROS), such as $O_2$.— or OH., which are produced during transferring an electron to mitochondrial oxygen, destroy the structure and components of mitochondria, causing changes in respiration rate and oxidative phosphorylation state, and consequently affecting ATP generation or NADH/NAD+ ratio that determines the cell metabolism. It is reported that most of the energy production in higher animals is attributed to ATP synthesized in the mitochondria, and the energy metabolism occuring in the mitochondria is closely associated with aging (Lee J W et al., *J Korean Med Assoc.* 52(10): 1007-19, 2009).

It is confirmed that ATP production in normal cells is increased by treatment of the luterion. The term "preventing aging-associated diseases or conditions" as used herein refers to reducing the occurrence thereof and delaying or reversing aging-related diseases.

The term "aging or aging cells" as used herein refers to cell cycle arrest in mitotic cells, which may be caused by telomere dysfunction, DNA damage, or oncogene activation. In germinated yeast, senescent cells induced by telomeric dysfunction are arrested in the G2/M phase of the cell cycle. In mammalian cells, senescent cells are arrested in the G0 phase, a non-mitotic phase outside the cell cycle. Aging in WI-38 fibroblasts refers to cells that do not increase in number during 10 days after passaging when observed under a microscope, and exhibit positive staining of β-galactosidase.

The term "cells after somatic cell division" as used herein refers to a group of cells that are suspended in the G0 group, a non-mitotoic phase outside the cell cycle, but whose primary function is maintained for the life of the remaining organism. The cells after somatic cell division include neuronal cells, cardiac muscle cells, and muscle cells. Some cell types of mature organisms, such as liver and kidney parenchymal cells, can enter the G0 phase semi-permanently and can be induced to start dividing again in very specific circumstances. These kinds of cells are considered as the cells after somatic cell division when they are in the G0 phase.

The diseases or conditions associated with aging are associated with loss of mitochondrial function, telomere dysfunction, senescence cell degeneration, age-dependent cell loss, or cell cycle arrest of cells after mitochondrial degeneration or somatic cell division.

In one exemplary embodiment, the luterion interacts with the telomerase enzyme and stimulates and/or increases telomerase expression and/or activity in the tissue or cells of the individual. In some exemplary embodiments, such activity may be reduced or absent, thereby resulting in the growth or development of the pathogen or syndrome associated with diseases. Such diseases or conditions include (a) Alzheimer's disease; (b) Parkinson's disease; (c) Huntington's disease; (d) seizures; (e) nerve damage, motor neuron diseases, multiple sclerosis (MS), peripheral and central nervous system injury (including spinal cord injury and stroke); (f) skin aging-related diseases such as skin atrophy and thinning, elastic fiber fusion, and skin wrinkles, sebaceous hyperplasia or hypoplasia, senile black spot, pigment defects, gray hair and hair loss or thinning (balding, hair loss) or chronic skin ulcers; (g) degenerative joint diseases; (h) osteoporosis, arthritis, and other degenerative symptoms of the skeletal system; (i) aging and stress-related diseases of the vascular system including atherosclerosis, calcification, thrombosis, hypertension, and aneurysms; (j) aging-related macular degeneration; (k) AIDS; (l) aging- and stress-related immune system damage including tissue turnover incidence, which occurs with natural aging, cancer, cancer treatment, acute or chronic infection, degenerative inflammatory disease or genetic disease causing accelerated cell turnover and associated anemia and other degenerative symptoms; (m) treatment of epidermal wounds, burns, abrasions, or other acute or chronic symptoms; (n) congenital keratinization abnormality; (o) sarcopenia and/or other muscular disorders or conditions; p) luteal defects; (q) premature ovarian failure (primary ovarian failure or hypogonadism); (r) damaged sperm production; (s) impaired sperm delivery; and/or (t) increase of telomerase expression and/or activity in memory T cells to enhance immune memory response and response to the vaccine; and/or (u) increase of the expression and/or activity of telomerase in healthy tissues to maintain the health of the individual while prolonging the life of the individual and/or clinical treatment and/or diagnostic fields, including any exemplary embodiment included in the term "treatment" as used herein.

EXAMPLES

Hereinafter, the present disclosure will be described in more detail with reference to Examples. It will be understood by those skilled in the art that these Examples are for illustrative purpose only and that the scope of the present disclosure is not construed as being limited to these Examples.

Example 1: Isolation of Luterion (1) Extract of Luterion 100 g of a medicinal plant, *Rhus verniciflua stokes*, was cut to fit into the container with size of 20 to 30 times the medicinal plant, i.e., container with a size of 2 to 3 liters, and placed in the container. 500 g to 800 g of distilled water (preferably 6 times of the plant, i.e., 600 g), which is 5 to 8 times the amount of the plant, was added to the container, and then boiling was conducted. Bubbling with oxygen for 20 to 30 minutes was performed about every 3 hours, so that the luterion of the plant was not entangled during the 8-hour boiling. The vaporized steam obtained from the boiling and bubbling was collected in a flask. The condensed liquid obtained by cooling and condensing the collected steam was irradiated with IR light (wavelength: about 3 μm to about 1000 μm, preferably 200 μm to 600 μm) for 1 hour to 2 hours to prevent mutation of the luterion and induce fission. Such process is illustrated in FIG. 37.

(2) Separation by Centrifugation and Filtering

The condensate collected in the step (1) was subjected to primary centrifugation at 190 g to remove the pelleted impurities, followed by secondary centrifugation at 3000 g and the stabilization for several minutes (preferably about two hours), and the supernatants thereof was collected. At this time, the luterion was stained with anti-CD332 tagged with fluorescence probe and then the presence of the luterion was firstly confirmed by checking its mobility via fluorescence imaging. Subsequently, the solution was subjected to a third centrifugation at 120,000 g in order to obtain pure luterion from the supernatant.

In detail, the filtrate after passage of the luterion through a filter with a size of 800 nm was centrifugation at 140,000 g or more to remove debris pellets such as exosomes or internal plants such as plasma, and then the pellet-free supernatant was collected. The supernatant was filtered with a 400 nm filter, and the filtrate was collected, followed by staining with a fluorescent anti-CD332 to confirm for the motility of the luterion. It was filtered with a 50 nm filter, and the unfiltered part trapped on the filter was collected to obtain the luterion and fixed at pH 1 or below −90° C.

By this process, the luterion having a diameter of the major axis between 50 nm and 800 nm was obtained, which was able to be observed through a dark-field microscope or a confocal microscope. The obtained luterion was classified into 50 nm to 200 nm (generating stage)/200 nm to 400 nm (maturing stage)/400 nm to 600 nm (splittering stage)/600 nm to 800 nm (oversplittering stage) depending on the sizes.

In the same manner, the luterion was obtained from the medicinal plants, *angelica gigas, rhois vernicifluae cortex*, and kiwifruit described in Tables 1 to 4.

(3) Separation by Surface Antigen-specific Antibody 3-1) Identification of Luterion Surface Antigen Anti-CD39 antibody (sc-18766, Santa Cruz Biotechnology), anti-CD73 antibody (sc-25603, Santa Cruz Biotechnology), or anti-CD332 antibody (BS-0675R, Bioss Inc) was bound to the luterion separated from the plants, and anti-FITC were bound thereto, to observe the florescence of the surface antigensof the luterion (blue fluorescence: CD133/1-VIOBRIGHT-FITC). Red fluorescence was obtained with PE (Phycoerythrin: Miltenyi Bitech GmbH) tagging. After staining with Mito-tracker, DAPI and Hoechst, the positive staining development was identified though a fluorescent microscope.

As a result, it was confirmed that anti-CD39 antibody, anti-CD73 antibody, anti-CD133 antibody or anti-CD332 bound to the luterion stained with mito-tracker, DAPI or Hoechst, thus, confirming the presence of CD39, CD73, CD133, or CD332 at the surface of the luterion (See FIGS. 29 to 32).

3-2) Preparation of Antibody-fixed Particles

Step 1. Preparation of Carbon-coated Iron (Fe) Magnetic Nanoparticles 0.5 mmol of iron acetylacetonate hydrate was placed in an erlenmeyer flask containing 10 mL of octyl ether, and a metal precursor solution was prepared with stirring. Then ultrasonic waves were irradiated to the solution at 20 kHz (50%) for 10 minutes using an ultrasonic wave irradiator. It was observed that the solution which was initially orange was changed to black brown over time as the metal precursor solution was irradiated with ultrasonic waves. This change indicates that the iron oxide ($Fe_2O_3$) magnetic nanoparticles were successfully produced. A large amount of ethanol was added to the mixed solution in which the iron oxide magnetic nanoparticles were prepared, and the resulting magnetic nanoparticles were precipitated. Then, the magnetic nanoparticles and the supernatant were separated by centrifugation and the supernatant was removed. After repeating the above washing process three times or more, the magnetic nanoparticles were dried at a temperature of 50° C. for 12 hours to prepare iron oxide magnetic nanoparticles having a size of 300 nm. The prepared iron oxide magnetic nanoparticles were heat-treated at 600° C. for 3 hours in an argon (Ar) atmosphere to obtain carbon-coated iron-magnetic nanoparticles.

Figure 33:
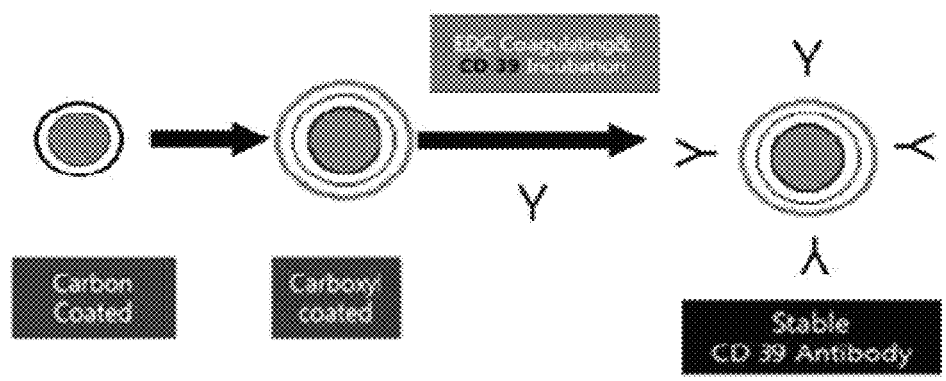
FIG. 33 shows a step of coating a bead with carbon and carboxy group followed by fixing an antibody that specifically binds to the luterion surface antigen to the coated particle.

Step 2. Preparation of Carboxyl Group-coated Magnetic Nanoparticles 0.5 g of the carbon-coated iron-magnetic nanoparticles obtained in Step 1 and 1 g of succinic anhydride were dispersed in 25 ml of ethanol together with 5 ml of silane polyethylene glycol carboxylic acid, followed by reaction for 24 hours. After the reaction was completed, the precipitate obtained by centrifugation was washed with ethanol, and then dried in a vacuum oven to obtain iron-magnetic nanoparticles dual-coated with carbon and carboxyl groups. The above dual coated particle production step is schematically shown in the front portion of FIG. 33.

Step 3. Preparation of Antibody-fixed Particles

Anti-CD39 antibody, anti-CD73 antibody, anti-CD133 antibody, or anti-CD332 antibody was thiolized by reaction with a thiol-reactive reagent. The iron magnetic nanoparticles having the carboxyl functional group prepared in Step 2 were reacted with an antibody having the thiol group to attach the antibody to the iron magnetic nanoparticles. The antibody-fixed particles are schematically shown in the back portion of FIG. 33.

3-3) Separation of Plant or Food-derived Luterion

Figure 34:
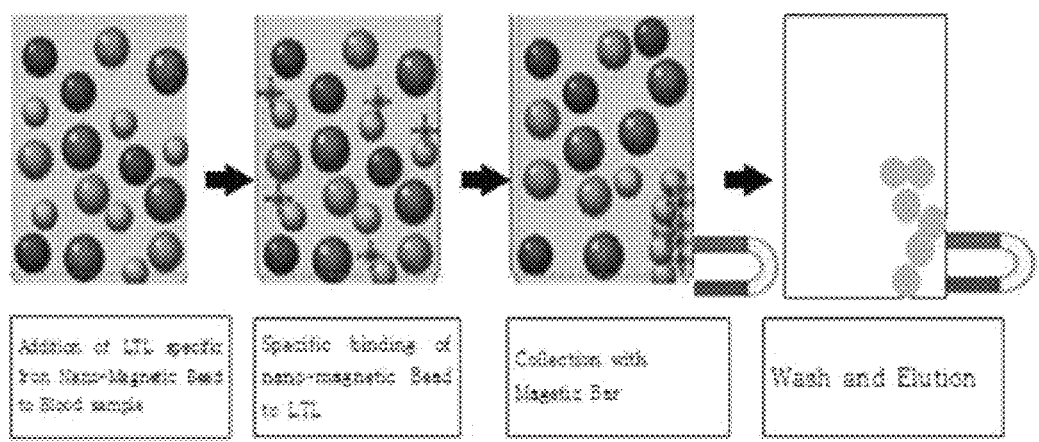
FIG. 34 shows a step of separating luterion from blood, by magnets, using a magnetic bead coated with an antibody that specifically binds to the luterion surface antigens.

100 μl to 200 μl of plant extracts and 5 μl of CD39 antibody-iron magnetic nanoparticles or CD73 antibody-iron magnetic nanoparticles were placed in a beaker to bind to each other for 30 minutes, and washed by placing them in a magnetic separator for 1 to 2 minutes to collect the luterion-magnetic nanoparticles and eliminate the supernatant. 0.033% (w/w) BSA (Bovine Serum Albumin)/PBS buffer solution was added to the iron-magnetic nanoparticles bound to the luterion and incubated at 25° C. for 1 hour, and then only BSA-adsorbed nanoparticles were separated using a magnetic bar. A certain amount of PBS was added again to the BSA-adsorbed iron-magnetic nanoparticles for desorption of BSA through incubation. The adsorbed BSA was quantitative-analyzed by FP-640 spectrofluorometer (JASCO) at 280 nm using standard calibration curve method (Emission slit: 0.5 nm, absorption slit: 0.5 nm). The separation of the plant luterion using the iron-magnetic nanoparticles is schematically shown in FIG. 34.

3-4) Identification of Separated Luterion

Figure 35:
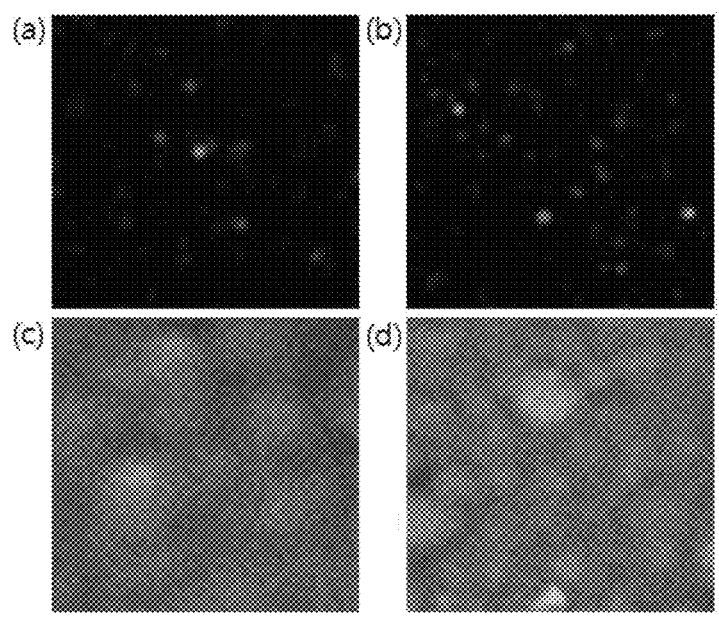
FIG. 35, panels (a) through (d), show images taken with a fluorescence microscope after separation of the luterion, wherein FIG. 35, panel (a) is an image of the luterion bound by fluorescent antibodies against CD39, CD73, CD133 and CD332 separated from Rhus verniciflua stokes extract using a nanofilter, viewed under the fluorescent microscope, FIG. 35, panel (b) is an image of the luterion obtained by separation using the magnetic beads bound by the fluorescent antibodies against CD39, CD73, CD133 and CD332 which specifically bind the surface antigens of the luterion, viewed underthe fluorescent microscope, FIG. 35, panel (c) is an image of the luterion separated using the nanofilters and viewed under the electron microscope, and FIG. 35, panel (d) is an image of the luterion obtained by separation using the magnetic beads bound by the antibodies that specifically bind the luterion surface antigens, viewed under the electron microscope.

Anti-FITC was bound to each of antibodies binding to CD39, CD73, CD133, or CD332 in each of the luterion separated from the above 3-3 and the luterion separated by the filtering of (2) to observe the presence or absence of positive fluorescence staining (See FIG. 35, panels (a) through (d)). The extraction yields of the two separation methods were compared through a fluorescence activated cell sorter.

Figure 36:
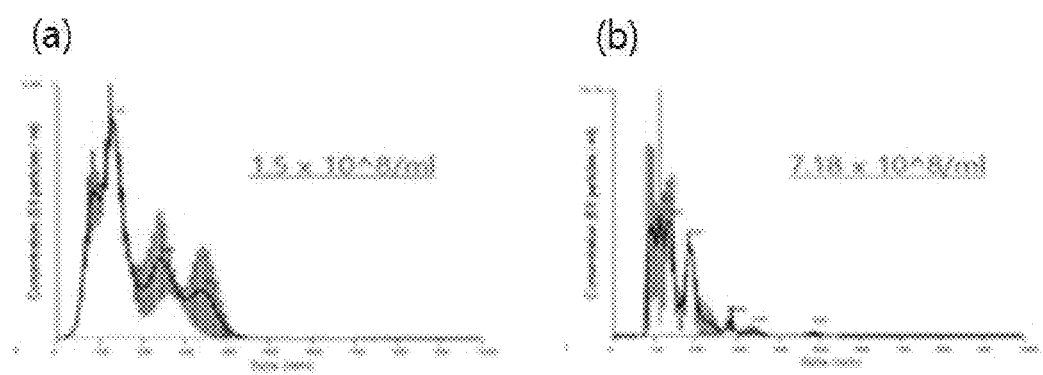
FIG. 36, panels (a) and (b), represent the number of the extracted luterions, wherein FIG. 36, panel (a) represents the number of the extracted luterions after their separation using a nanofilter, and FIG. 36, panel (b) represents the number of extracted luterions after their separation using a magnetic bead on which the antibodies that specifically bind to the luterion surface antigens are bound.

As a result, in the case of separation using nanofiltering method, the number of the luterion was $1.5 \times 10^8$/ml, whereas in the case of separation using particles binding to CD39, CD73, CD133, or CD332 surface antigen, the number of the luterion was $7.18 \times 10^8$/ml. The number of the luterion thereof was four times or more as compared with the nanofiltering method (See FIG. 36, graphs (a) and (b)).

TABLE 5

| Separation method of luterion | 50~400 nm luterion extraction efficiency ratio | loss rate |
|---|---|---|
| (2) nano-filtering method | 40~45% | 50~60% |
| Separation using antibodies | >90~95% | <10% |

As illustrated in Table 5, it was confirmed that when the nano-filtering method was used, the final extraction efficiency ratio of the luterion having a size of 50 nm to 400 nm is 40% to 45%, and the loss rate is 50% to 60%, while the separation using the antibody-iron nanoparticles binding to CD39, CD73, CD133, or CD332 surface antigen of the present disclosure resulted in the final extraction efficiency ratio of 90% to 95% or more, and the loss rate being 10% or less. This result confirmed that the extraction efficiency ratio was significantly higher with the antibody-iron nanoparticle separation method.

From these results, it was confirmed that the separation method using the antibody or aptamer-fixed particles that bind to the luterion surface antigen of the present disclosure increased the final extraction ratio and decreased the loss rate during the separation process in comparison with the conventional luterion separation method using the nanofilter.

(4) Confirmation of Difference Between Plant Mitochondria and Luterion

As illustrated in Table 6, it was confirmed that the plant mitochondria did not express any surface antigens of CD332, CD39, CD73, CD133, and CD326. In addition, when they were centrifuged at over 140,000 g, the mitochondria burst out, but the luterion maintained the shape thereof. Further, it was confirmed that when applying more than 35,000 psi of pressurization to induce the fission, the mitochondria burst out, but the luterion maintained in shape thereof.

TABLE 6

| Category | CD332 | CD39 | CD73 | CD133 | CD326 | Centrifuge Spin >140,000 g | French Press >35,000 psi |
|---|---|---|---|---|---|---|---|
| plant mitochondria | X | X | X | X | X | X burst out | X burst out |
| luterion | O | O | O | O | O | O maintained | O maintained |

Example 2: Fixation of Luterion

The luterion with motility and the luterion containing CD39, CD73, CD133, or CD332 as surface antigen were fixed, and then the number of the luterion was counted. IR was irradiated to identify the attracted luterion. The number of the luterion bound by the primary antibodies against CD332, CD39, CD133 or CD73 and the secondary antibody tagged with FITC were counted. Also the number of the luterion stained with the mito-tracker were counted. During this process, the luterion was fixed under the pH of 1 to 3, with temperature of −90° C. to 0° C. The results of the number counting in different pH and temperature conditions is shown in Tables 7 and 8 below (wherein + refers to the number of the counted luterion).

TABLE 7

| | 1 month | 2 months | 3 months |
|---|---|---|---|
| pH 1 | +++ | +++ | +++ |
| pH 3 | +++ | +++ | +++ |
| pH 5 | +++ | +++ | ++ |
| pH 7 | ++ | ++ | + |

TABLE 8

| | 1 month | 2 months | 3 months |
|---|---|---|---|
| RT (37° C.) | +++ | ++ | + |
| 0° C. | +++ | +++ | +++ |
| −90° C. or less | +++ | +++ | +++ |

As illustrated in Tables 7 and 8, it was confirmed that under the conditions of pH 1 to 3 and the temperature of −90° C. to 0° C., the luterion was preserved over 1 to 3 monthsin a fixed state without being affected in their numbers.

Example 3: Fission Inducement of Luterion Using Pressurization

Pressure was applied to the luterion separated in Example 1 through a french press as shown in Table 9 as below. Further, the influence of the temperature on the luterion fission was confirmed (+ indicates the extent of the fission).

TABLE 9

| | 5,000 | 10,000 | 15,000 | 25,000 | 35,000 | 35,000 or more |
|---|---|---|---|---|---|---|
| 0-10° C. | +++ | +++ | ++ | ++ | ++ | + |
| 10-20° C. | +++ | +++ | +++ | +++ | +++++ | + |
| 20-25° C. | +++ | +++ | ++ | ++ | ++ | + |

Figure 11:
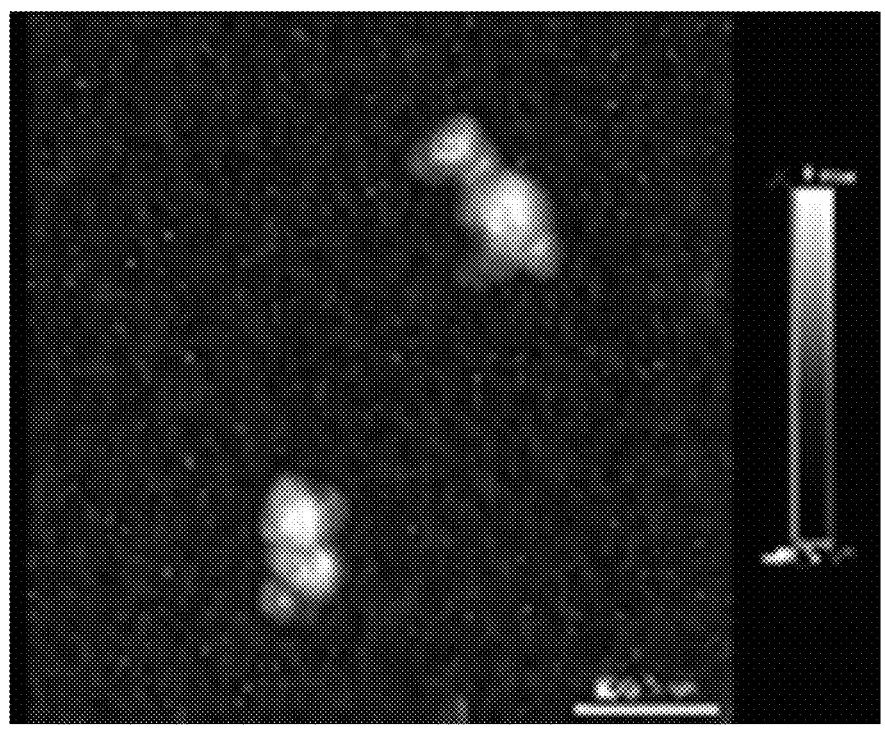
FIG. 11 shows the results of the induced fission of the luterion under the pressure of 5,000 psi and the temperature between 10° C. to 20° C.
Figure 12:
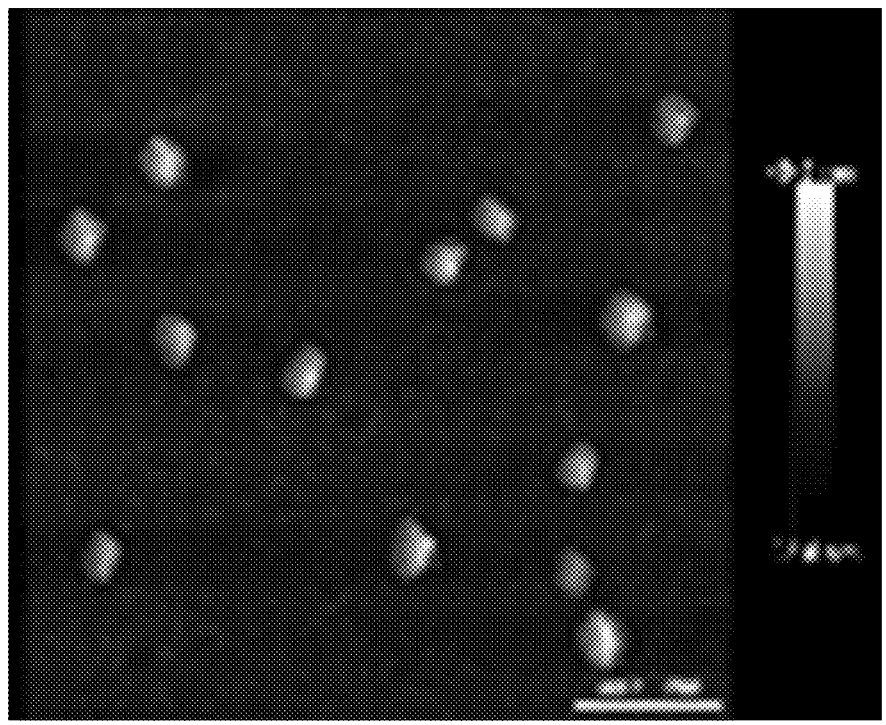
FIG. 12 shows the results of the induced fission of the luterion under the pressure of 15,000 psi and the temperature between 10° C. to 20° C.
Figure 13:
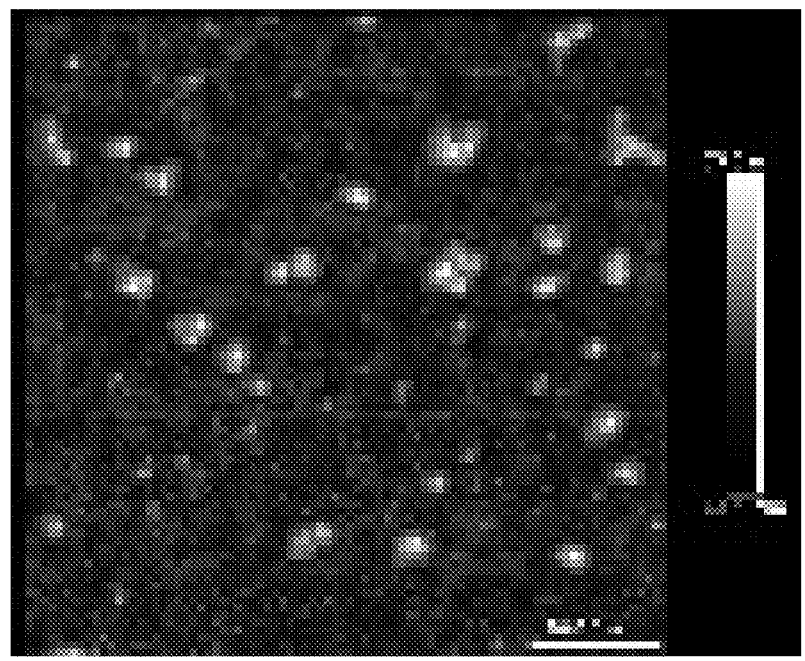
FIG. 13 shows the results of the induced fission of the luterion under the pressure of 35,000 psi and the temperature between 10° C. to 20° C.

According to Table 9 and FIGS. 11 to 13, it was confirmed that the fission was induced to proliferate the luterion at pH 1 to 3, pressure at 25,000 psi to 35,000 psi, and temperature at 10° C. to 20° C.

Example 4: Characteristics of Luterion (1) Structure

The luterion having a size of about 50 nm to about 400 nm of the luterion obtained in Example 1 was observed with a confocal laser scanning microscope (Zeiss), a transmission electron microscope, a scanning electron microscope, an atomic force microscope, and a confocal scanner (Leica TCS-SP8) to confirm that the luterion also has a membrane structure with a double membrane or multi-membrane similar to that of the mitochondria, in which the inner cristae structure is not completed, and it was observed in the same laser wavelength range as mitochondria. Also, it was observed that the shape of the luterion is circular or oval (See FIG. 6).

Further, the image of the luterion separated in Example 1 was capture from a transmission electron microscope. As a result, it was confirmed that the luterion had a double membrane or multi-membrane structure as shown in FIG. 8.

(2) Staining Properties

The luterion having a size of about 50 nm to about 800 nm of the luterion obtained in Example 1 was stained with Mito-tracker, Rhodamine 123, Janus green B, respectively and the presence or absence of staining was observed. As a result, it was confirmed that the staining was positive with the mitotracker, Rhodamine 123, and Janus green B (See FIGS. 2, 3, and 5).

(3) Autofluorescence

Figure 4:
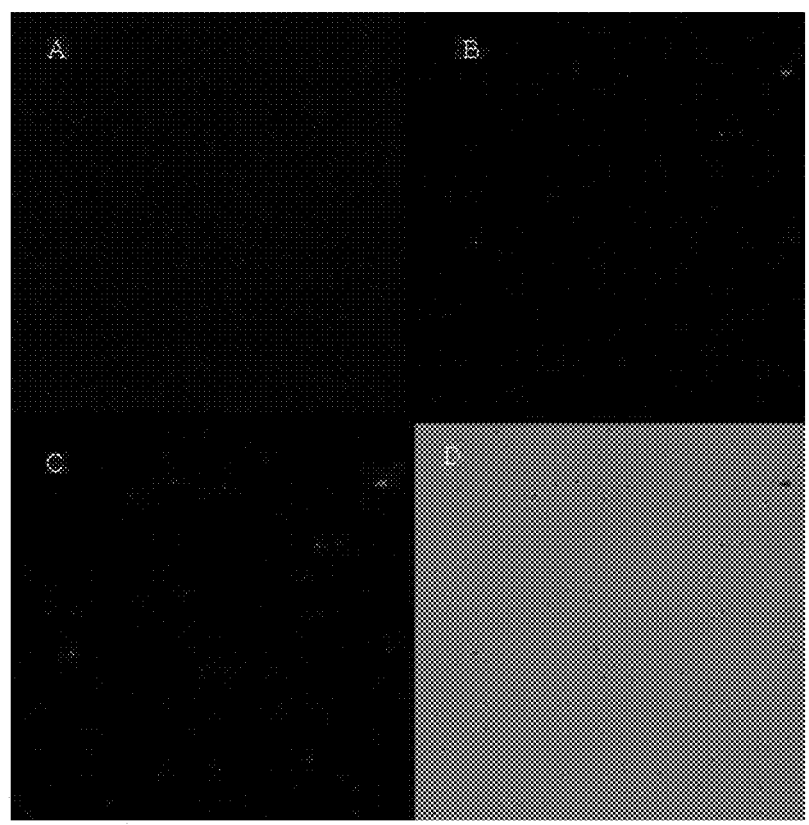
FIG. 4 illustrates comparisons of fluorescence/non-fluorescence images of the luterion (A: Janus Green B Positive, B: Rhodamine 123 Positive C: Mito-tracker Red Positive; and D: no staining).
Figure 5:
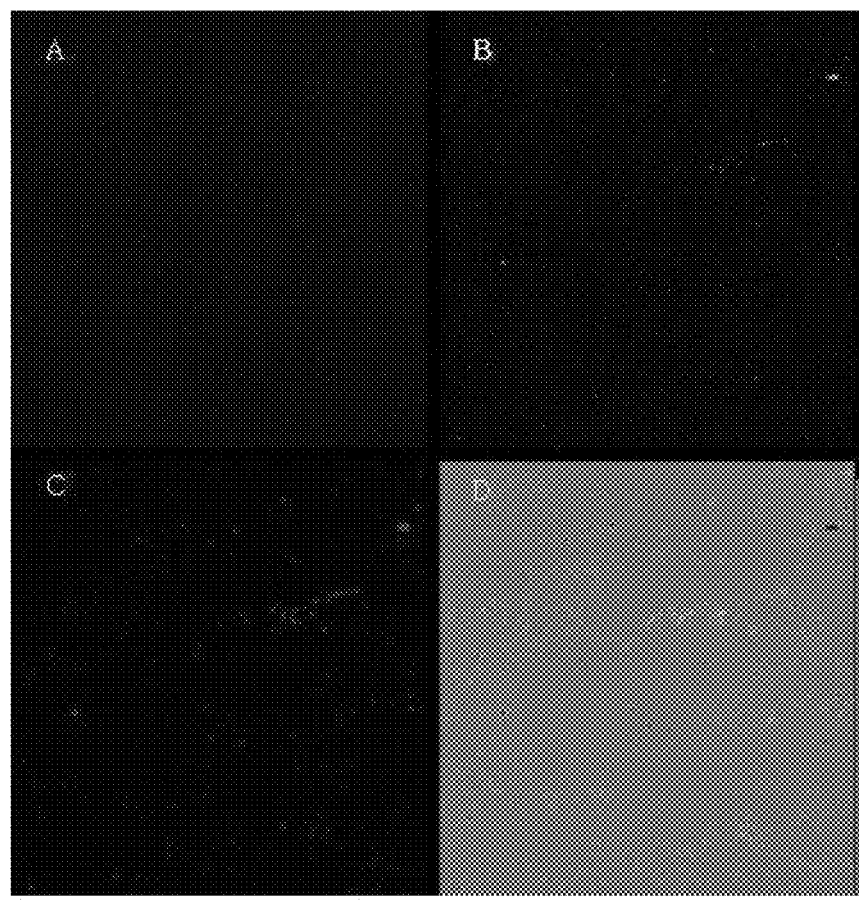
FIG. 5 illustrates whether the luterion co-stains with Rhodamine 123, Mito tracker red, and Janus green B (A: Janus Green B Positive, B: Rhodamine 123 Positive C: Mito-tracker Red Positive; and D: no staining).
Figure 6:
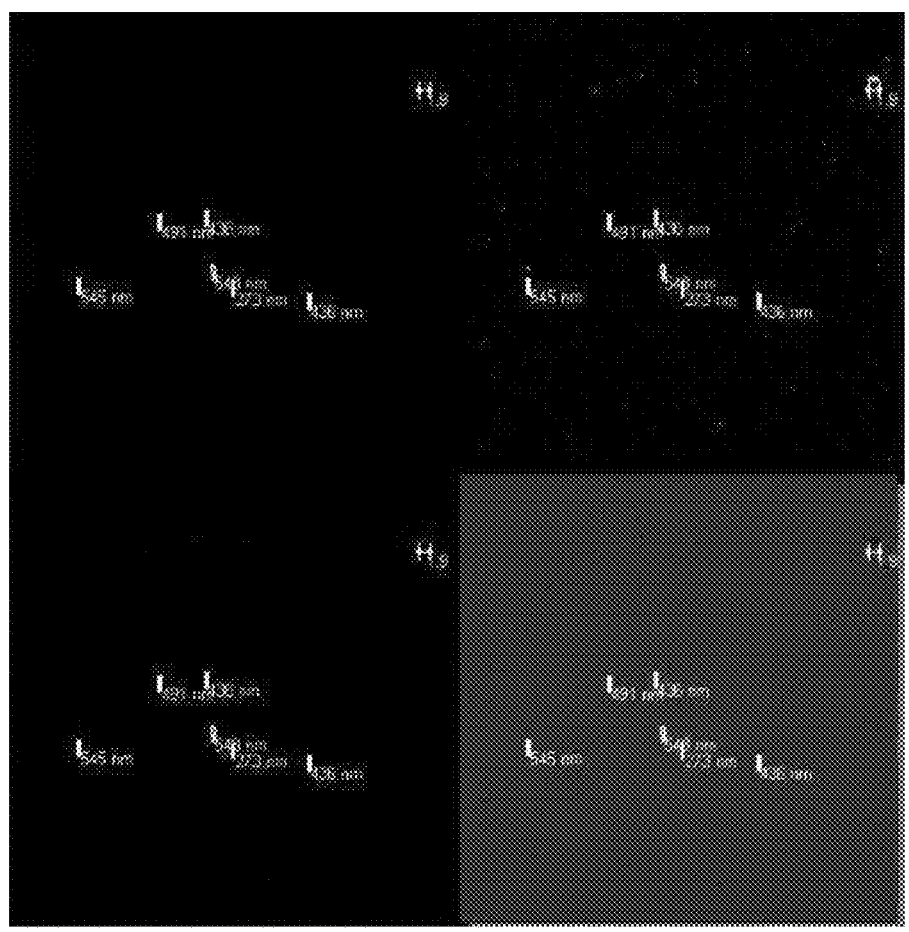
FIG. 6 shows the size (50 nm to 800 nm) of luterion by measuring the size of the fluorescence stained region of the luterion (A: Janus Green B fluorescence size measurement; B: Rhodamine 123 fluorescence size measurement; C: Mito-tracker red flurescence size measurement: D: no fluorescence size measurement).
Figure 7:
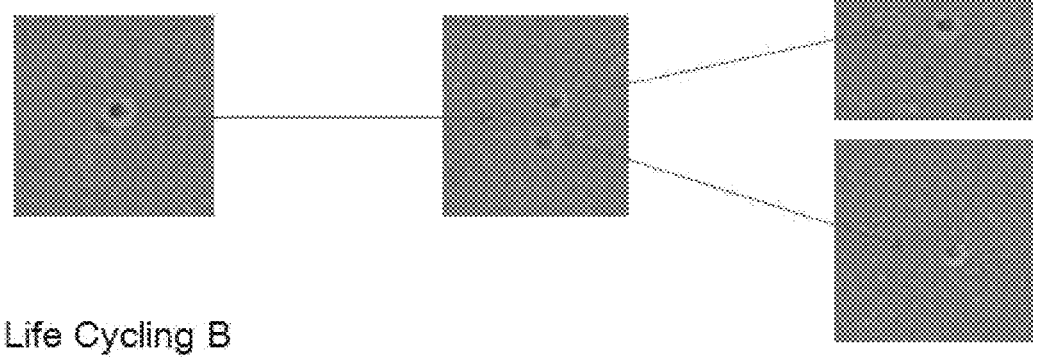
FIG. 7 shows life cycle A of normal luterion and life cycle B of mutated luterion.
Figure 7:
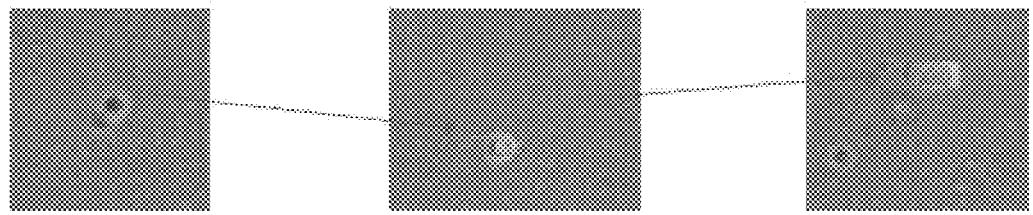

It was confirmed that the luterion having a size of about 50 nm to about 800 nm of the luterion obtained in Example 1 exhibited a light response as observed in fluorescent photographs (See FIG. 4).

(4) Analysis of Presence of RNA in Luterion

As a result of an atomic microscope imaging of the luterion having a size of 200 nm to 400 nm separated in Example 1, it was able to be presumed that a nucleic acid such as RNA or DNA is contained in the luterion, as shown in FIG. 9.

QIAGEN kit (AllPrep DNA/RNA micro kit: Cat 80284) was used to separate total RNA and DNA from the 200 nm to 400 nm luterion separated in Example 1, and then the final product was quantified using Experion RNA (DNA) StdSens (Bio-Rad) chip.

After centrifugation (8000 g, 90 minutes) and collection of the luterion, 3.5 µl of β-mercaptoethanol and 50 µl of the degradation buffer RLT plus (Guanidine isothiocycanate, detergents) contained in the kit were mixed with the collected luterion andand the resultant sample was passed through a syringe with 20 gauge needle 5 to 10 times to homogenize the luterion. The sample degradation buffer was transferred to AllPrep DNA spin column and then centrifuged (≥8000 g, for 15 seconds) to separate the DNA laid on the column from the buffer containing RNA that passed through the column.

First, 350 µl of 70% ethanol was added to the same volume of the buffer that passed through the column, mixed well, and then 700 µl of the mixture was transferred to RNease MinElute spin column, centrifuged (≥8000 g, for 15 seconds), and the buffer that passed through the column was removed. Column washing was performed sequencially using 700 µl of RW1, 500 µl of RPE buffer, and 80% ethanol, respectively. All centrifugation (≥8000 g, for 15 seconds) as used herein was performed under the same conditions. To obtain RNA, 14 µl of RNeasy-free solution was added to the column, followed by centrifugation (≥8000 g, for 60 seconds) to isolate the luterion RNA.

Figure 10A:
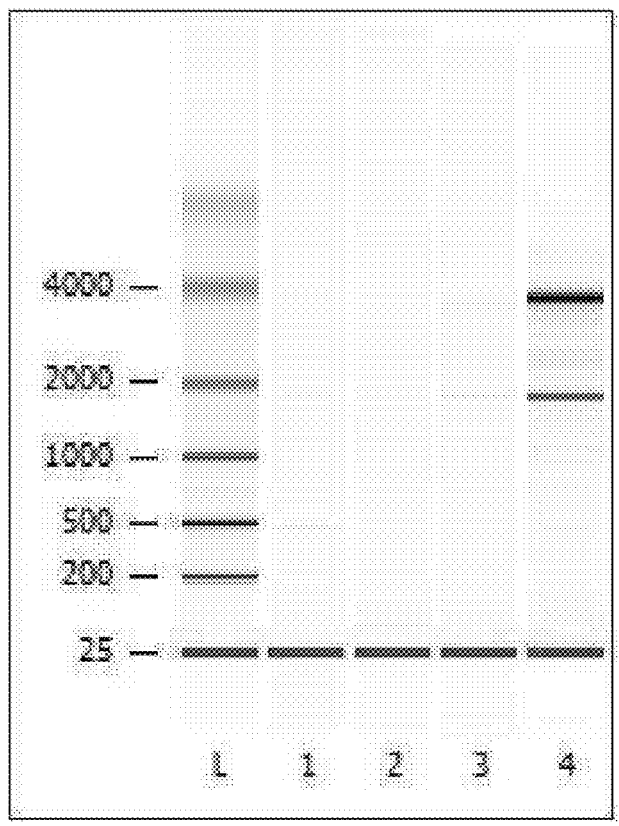
FIG. 10A is a bioanalyzer result obtained from analyzing whether RNA is contained in the luterion (L: Control; 1: 50 nm or less, 2: 50 nm to 100 nm, 3: 100 nm to 200 nm, 4: 200 nm to 400 nm).
Figure 10B:
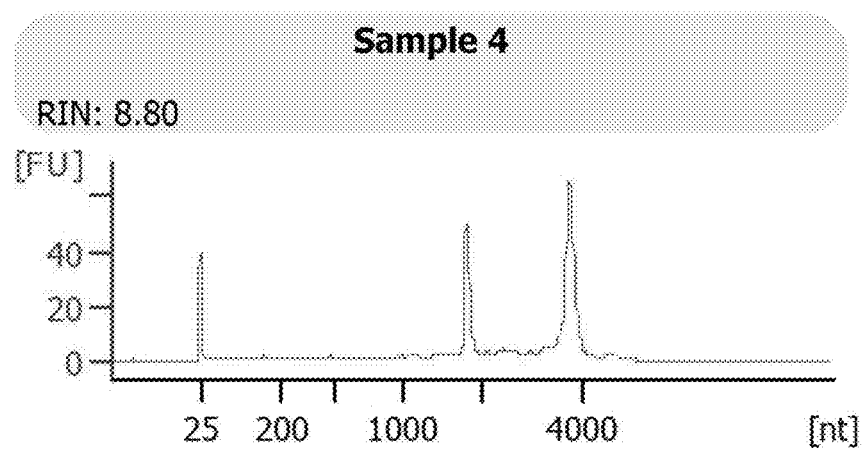
FIG. 10B shows total RNA of the luterion having the size of 200 nm to 400 nm.

In the first step for genomic DNA, DNA attached to the AllPrep DNA spin column was washed with each of 500 µl of AW1 and 500 µl of AW2 buffers. All centrifugation (≥8000 g, for 15 seconds) speed and time used as described above for the RNA isolation. After putting 50 µl of EB buffer into the column, it was left at room temperature for 2 minutes to 5 minutes and centrifuged (≥8000 g, for 60 seconds) to isolate the luterion DNA. As a result of quantification using Experion RNA (DNA) StdSens (Bio-Rad) chip, it was confirmed that RNA was contained in the luterion as shown in FIGS. 10A and 10B and DNA was also contained in the luterion. In particular, it was confirmed that RNA and DNA were contained in 200 to 400 nm luterion.

Example 5: Culture of Luterion (1) PBS was added to the luterion having about 50 nm to 200 nm in size obtained in Example 1, irradiated with IR light, and cultured at 18° C. to 30° C. for about 3 hours Immediately after irradiation of the IR light, the size of the luterion was observed with a microscope at intervals of about 1 hour. After about 1 hour to about 6 hours, it was confirmed that the luterion having a size of about 200 nm before cultivation was grown to about 500 nm. As a result, it was found that when water was added to the luterion and cultured at 18° C. to 30° C. under IR light irradiation, the size could be grown up to about 500 nm.

(2) PBS was added to the luterion having about 400 nm to 800 nm in size obtained in Example 1, irradiated with IR light, and cultured at 18° C. to 30° C. for about 3 hours Immediately after irradiation of the IR light, the size and the state of the luterion were observed with a microscope at intervals of about 1 hour. After about 1 hour to about 6 hours, it was confirmed that the luterion having a size of about 400 nm to about 800 nm before cultivation was not grown in its size but instead underwent fission.

(3) The luterion was cultured at pH of 7 and temperature of 20° C. using a medium (DMEM or blood culture medium) supplemented with glucose having a concentration of 5%. IR was irradiated to detect the gathered luterion. Luterion was bound to anti-CD332, anti-CD73, anti-CD133 and anti-CD39 antibodies, respectively, and then bound to the secondary antibodies tagged with FITC. Thereby, the number of the luterion showing fluorescence was counted. Further, the number of the luterion stained with the mitotacker was counted. The results are shown in Table 10 below (+ indicates the relative ratio of luterion number).

TABLE 10

|  | Before Culture | 3 weeks |
| --- | --- | --- |
| *angelica gigas* | + | +++ |
| *rhois vernicifluae cortex* | + | +++ |
| kiwifruit | + | +++ |

Example 6: Identification of Introducing Luterion inside Cells

Figure 15:
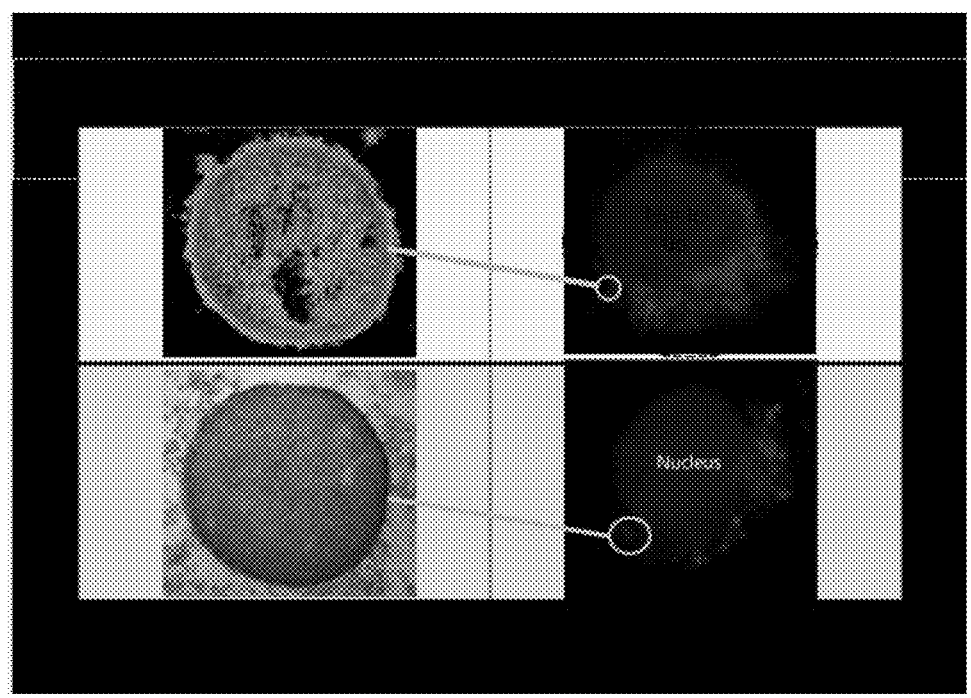
FIGS. 15 and 16 show results obtained by enlarging the stained image of the luterion entered into the cell (red: luterion, blue: cellular nucleus, outer red dotted circle: cell boundary).
Figure 16:
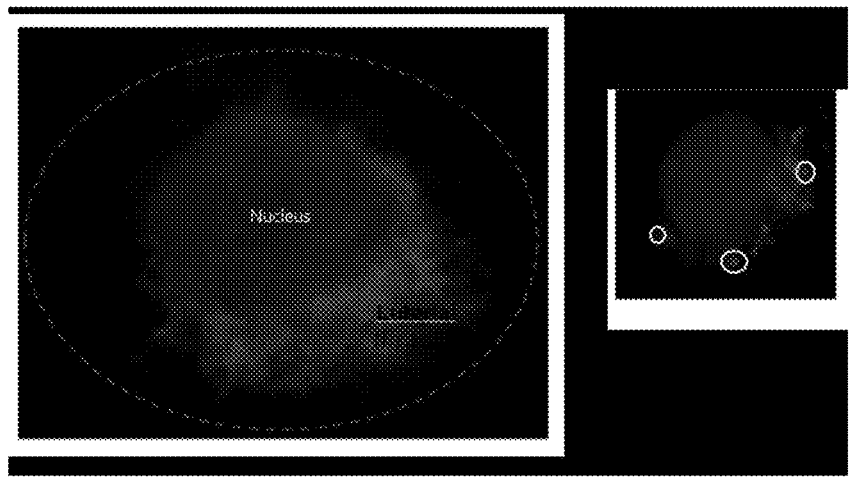

The luterion was fluorescently stained with PKH26-1, PKH26-2, and PKH26-3 red fluorescence, respectively, and incubated with A549 non-small cell lung cancer cells (ATCC #: CCL-185) for 24 hours. The cells were fixed and the morphology was observed with a microscope. The results are shown in FIGS. 14 to 16.

Figure 14:
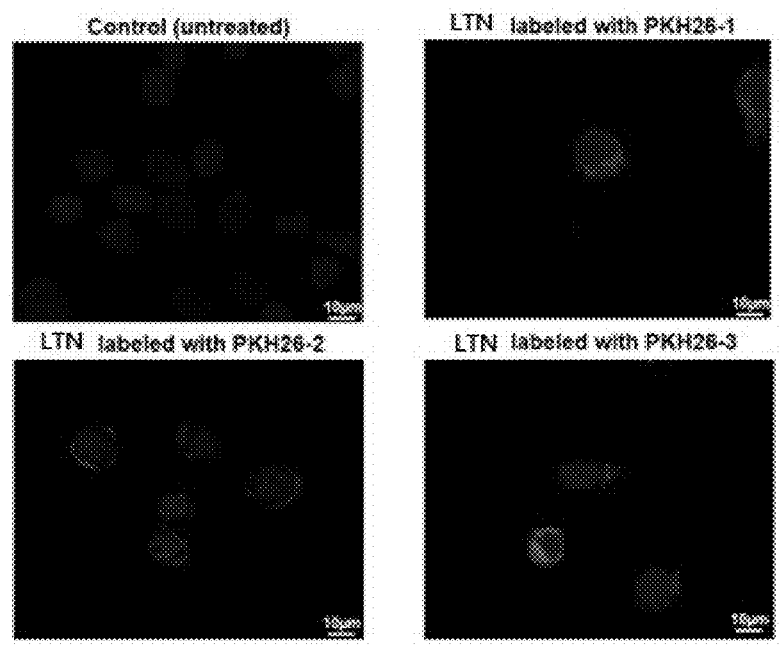
FIG. 14 shows the results of introducing the luterion into the cells after staining the luterion with PKH26-1, PKH26-2, and PKH26-3 fluorescence dyes (red) and staining the cellular nucleus with DAPI (blue).

Referring to FIG. 14, the luterion stained with PKH26-1, PKH26-2, and PKH26-3 in red was found to be introduced into the cell surrounding the DAPI-stained intracellular nucleus. The enlarged images in FIGS. 15 and 16 further confirmed the entry of the luterion into the cell.

Example 7: Identification of Passing Through Blood-brain Barrier (BBB)

Figure 17:
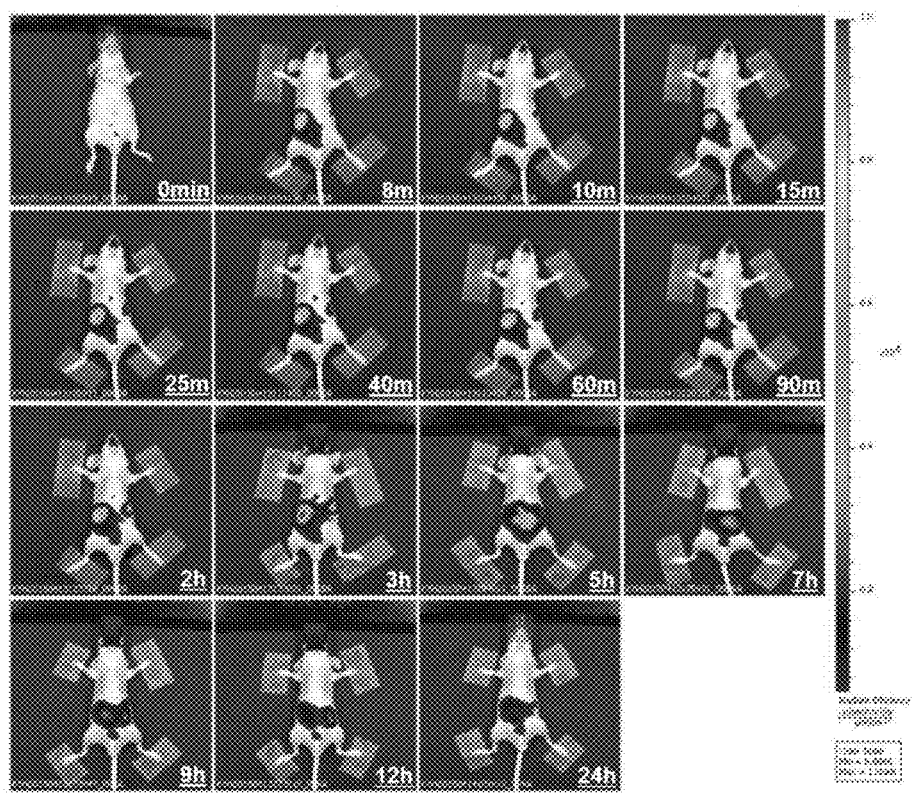
FIG. 17 shows the results of oral gavage administration of blue fluorescent luterion stained in blue with PKH26-1.

Mice were injected intraperitoneally (IP) or through oral gavaging with the fluorescent luterions stained with PKH26 to confirm whether the administered luterion passed through BBB. According to FIG. 17, it was able be confirmed that the luterion passed through BBB on oral gavage after at least 3 hours.

Figure 18:
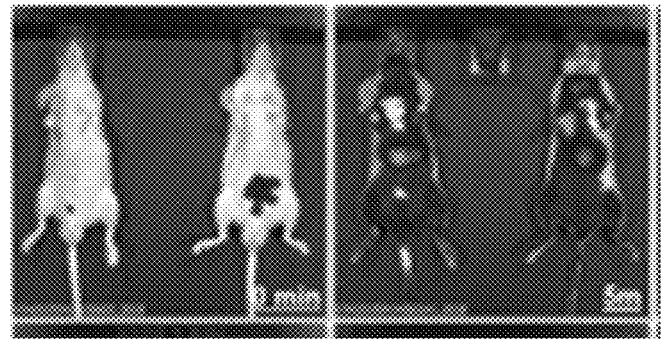
FIGS. 18 and 19 show the results of intraperitoneal injection of fluorescent luterion stained in blue with PKH26-1.
Figure 19:
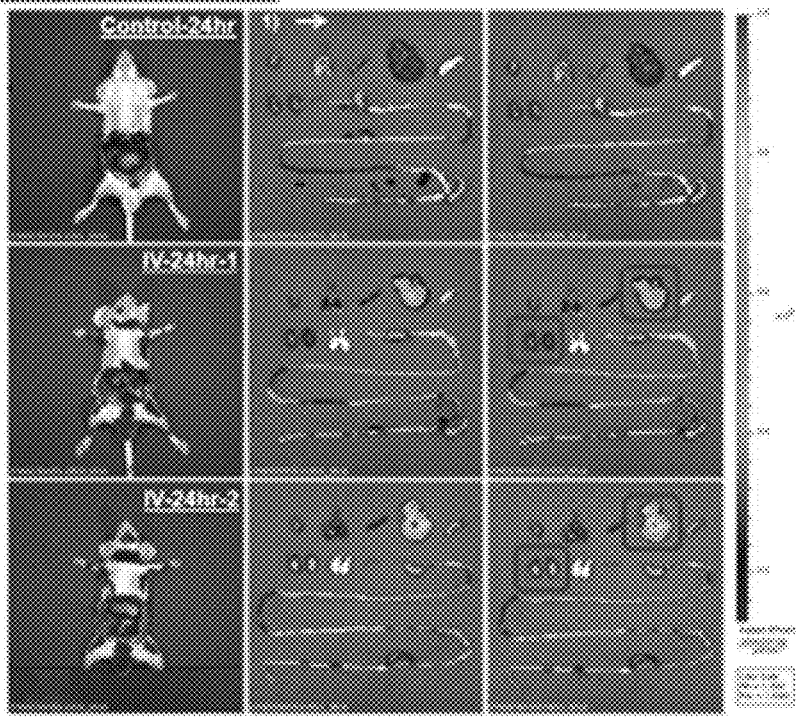

According to FIG. 18, it was able to be confirmed that the luterion passed through BBB within 5 minutes upon the intraperitoneal injection. According to FIG. 19, it was able to be seen that even after 24 hours from the intraperitoneal injection, it was distributed in the heart, lung, spleen, liver, pancreas, kidney, testis, abdomen, and whole body.

Example 8: Identification of Anti-cancer Effect of Luterion (Telomere/Telomerase Activity)

(1) Inhibition of Telomerase Activity of Cancer Cells $1 \times 10^6$ cells/ml of normal cells (Fibroblast) and cancer cells (NCl-H1975, MDA-MA-468, WiDr), respectively, were inoculated on 60 mm plates, and after about 12 hours, the luterion isolated in Example 1 was treated in a concentration of 50 μg/ml and cultured. Cell culture was performed in an incubator at 37° C. and 5% $CO_2$ under 1% FBS in the absence of antibiotic PSF (antibiotic-antimycotic). Each cell was harvested 48 hours after cell inoculation using 1% FBS DMEM medium to obtain telomerase activity.

Figure 20:
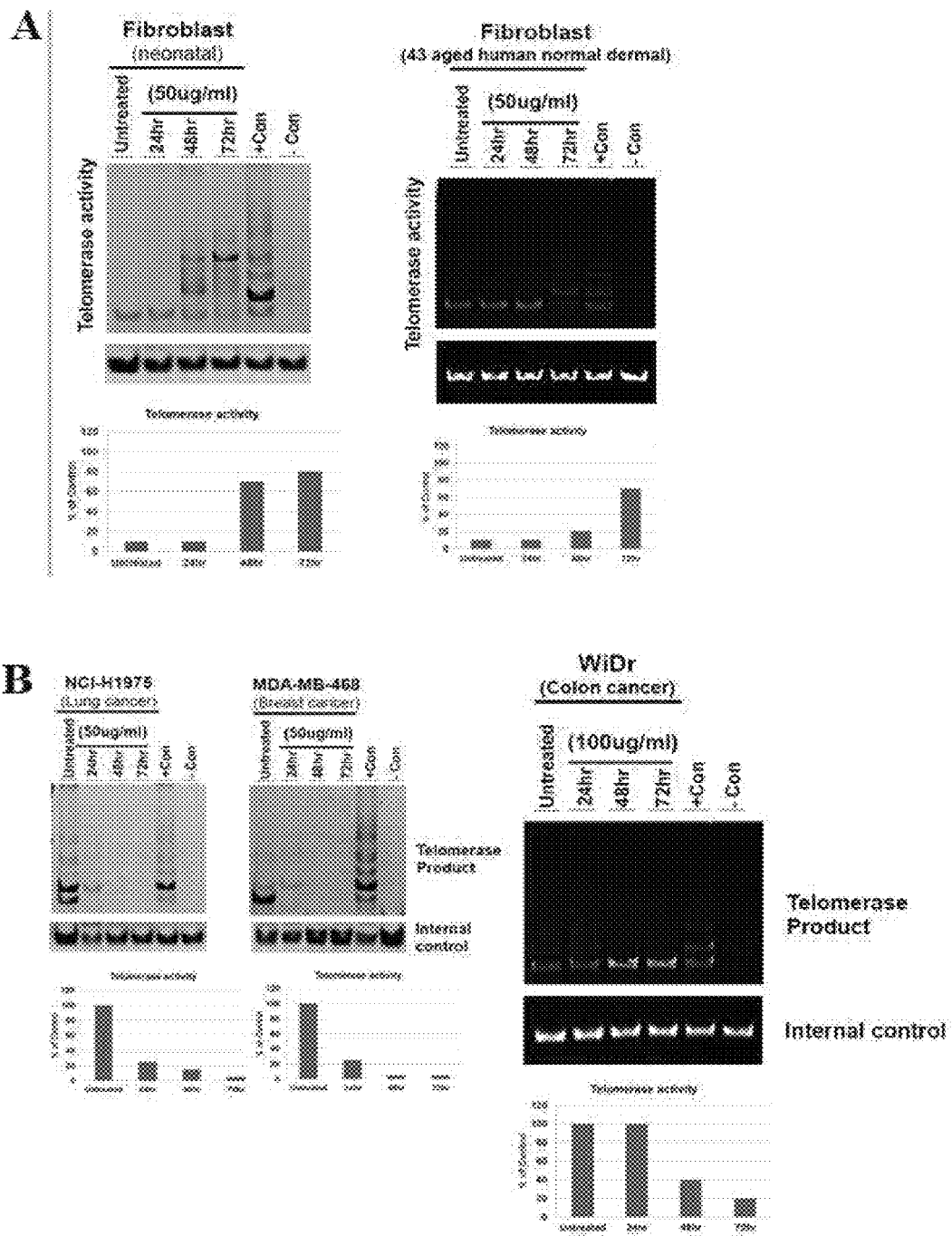
FIG. 20 shows telomerase activity in normal cells (Fibroblast) and cancer cells (lung cancer, breast cancer, colon cancer) after the luterion treatment.

Analysis of telomerase activity by TRAP assay (TRA-Peze® Telomerase Detection Kit (Millipore)) revealed that telomerase expression and activity of the cancer cells (NCl-H1975, MDA-MA-468, WiDr) was decreased by the luterion treatment (See FIG. 20B).

Further, as a result of performing the same experiment and analysis on normal cells, Fibroblast, it was confirmed that telomerase expression and activity were increased in human normal cells as compared with the control group (group untreated with the luterion group) (See FIG. 20A).

(2) Inhibition of Proliferation of Cancer Cells by Treatment with Luterion

MTT assay was performed to measure the luterion's cytotoxicity against cancer cells in several types of human cancer cell lines (lung cancer (NCl-H1975), colon cancer (WiDr), breast cancer (MDA-MB-486), liver cancer (HCC38), and leukemia (AGH-77)) and normal cell lines (fibroblast).

10 μl of cell suspension of $5 \times 10^4$ cells/ml ($8 \times 10^3$/well) were inoculated into each well of a 96-well having microtiter plate with a flat bottom and cultured for 24 hours, and then replaced with medium containing various concentrations of the luterion and cultured for another 48 hours. Then, 100 μl of a non-aqueous yellow MTT (3-(4,5-dimethylthiazole-2-yl)-2,5-diphenyltetrazolium bromide) solution diluted 10 times with the medium was added to each well. The cells were stored in an incubator at 37° C. and 5% $CO_2$ concentration to produce formazan crystals. After about 4 hours, the extra medium was removed, and 200 μl of DMSO was added to each well to dissolve the water-insoluble formazan formed in the cells, and then the absorbance was analyzed at 595 nm using a microplate reader.

Figure 21:
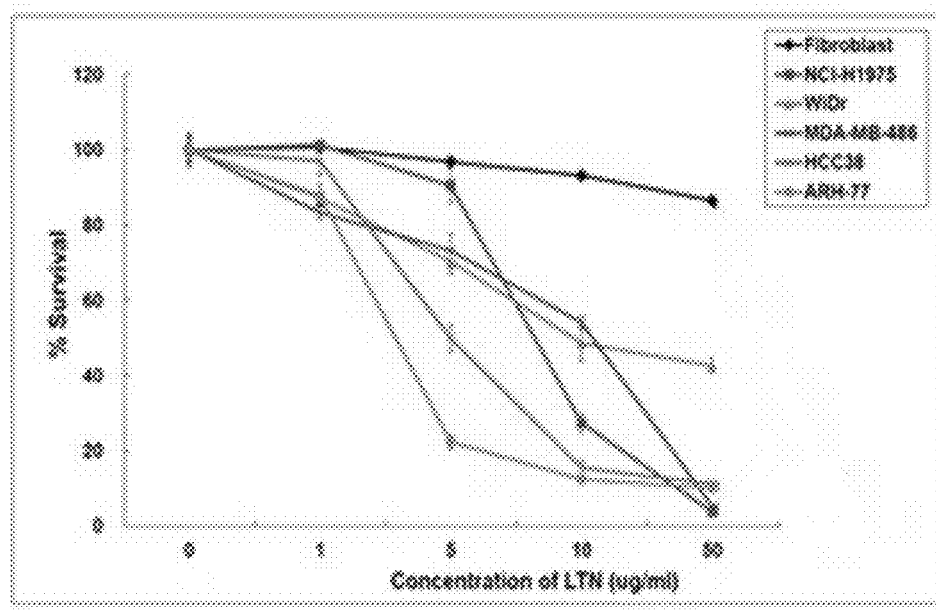
FIG. 21 shows cell viability of normal cells (Fibroblast) and various cancer cells (lung cancer, breast cancer, colon cancer, liver cancer, leukemia) after treating with vaious concentrations of luterion.

The survival rate of cancer cells at each concentration was measured as 100% of the absorbance of the control group not treated with the luterion, and the survival rate of cancer cells was decreased in a concentration-dependent manner On the other hand, there was no cytotoxicity in normal cells (See FIG. 21).

Figure 22:
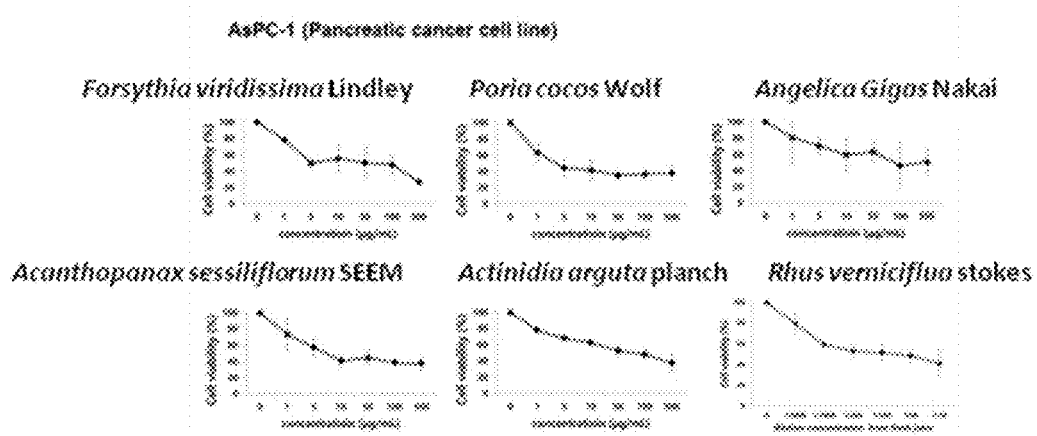
FIG. 22 shows inhibition of cell proliferation in a pancreatic cancer cell line (AsPC-1) treated with variously derived luterion.
Figure 23:
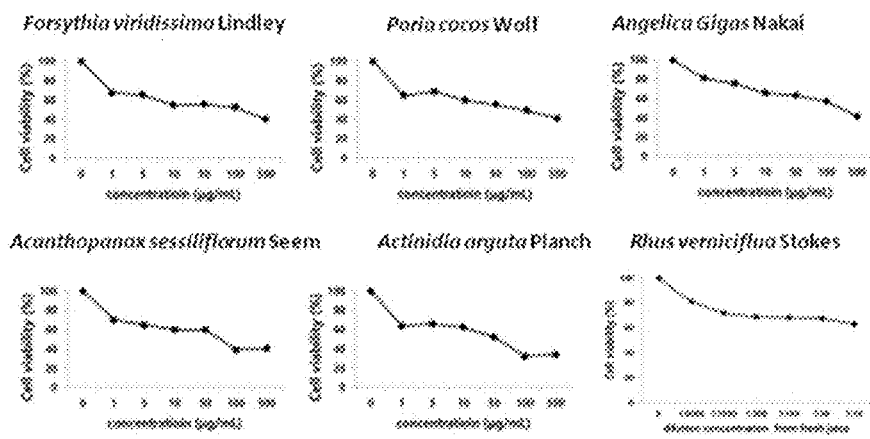
FIG. 23 shows inhibition of cell proliferation in a lung cancer cell line (A549) treated with variously derived luterion.
Figure 24:
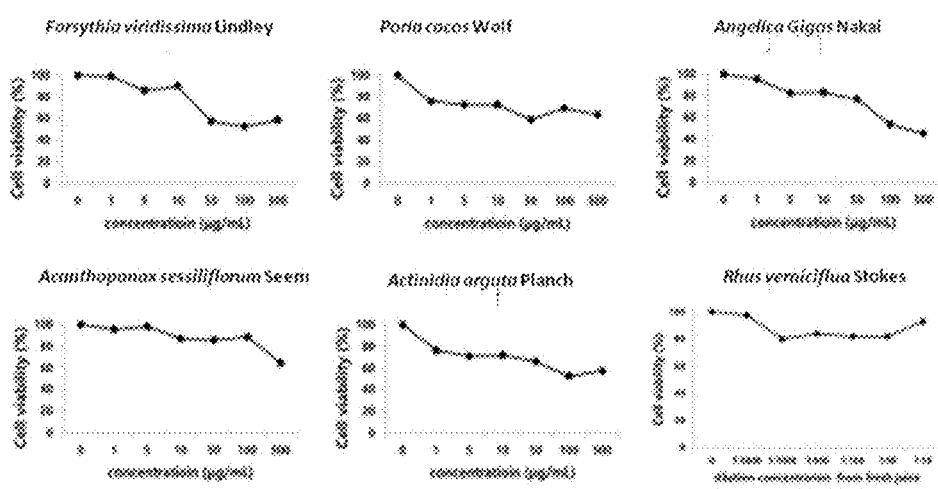
FIG. 24 shows inhibition of cell proliferation in a breast cancer cell line (BT-20) treated with variously derived luterion.

In addition, the cancer cell proliferation inhibitory effect of variously derived luterion in the AsPC-1 pancreatic cancer cell line, A549 lung cancer cell line, and BT-20 breast cancer cell line was confirmed in addition to the above cancer cell lines. The cell viability was measured in the same manner as in the MTT assay described above, and the variously derived luterion isolated by the method of Example 1 showed cell proliferation inhibitory effect on cancer cells (FIGS. 22 to 24).

Therefore, it was found that the luterion of the present disclosure can prevent or treat a cancer by inhibiting the proliferation of cancer cells.

Example 9: Increase of Telomerase Activation in Normal Cells by Luterion $1 \times 10^6$ cells/ml of normal cells (Fibroblast) were inoculated on 60 mm plates, respectively, and after about 12 hours, the luterion isolated in Example 1 was added to each well at a concentration of 50 μg/ml. Cells were cultured in an incubator at 37° C. and 5% $CO_2$ using 1% FBS DMEM medium in the absence of antibiotic PSF (antibiotic-antimycotic). Cells were harvested 48 hours after inoculation, and telomerase activity was measured.

Figure 25:
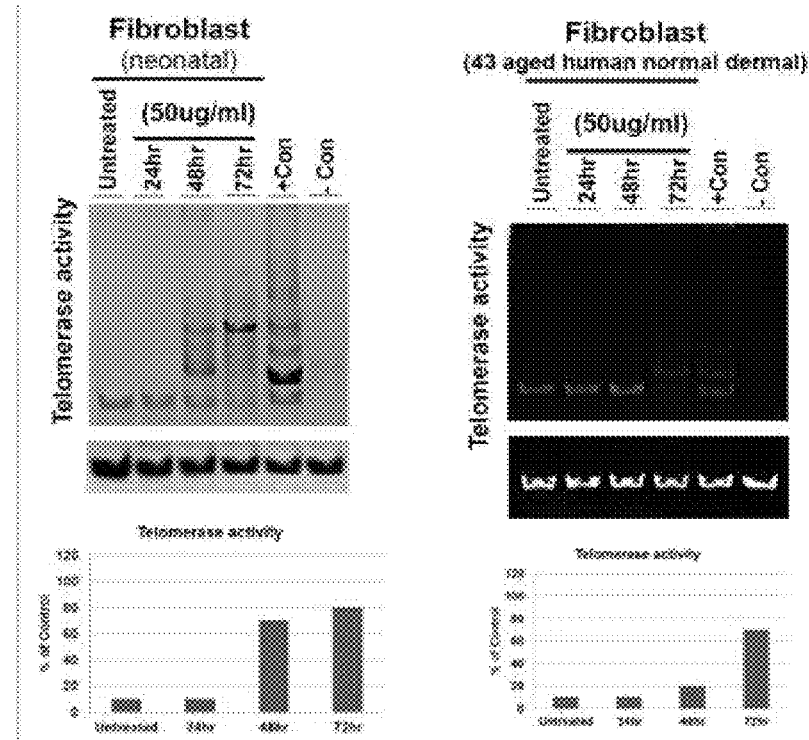
FIG. 25 shows telomerase activity in normal cells (Fibroblast) after the treatment with the luterion.

Analysis of telomerase activity by TRAP assay (TRA-Peze® Telomerase Detection Kit (Millipore)) revealed that telomerase expression and activity of the normal cells, Fibroblast, was increased by the luterion treatment (See FIG. 25).

Example 10: Effect on ATP Production by Luterion

Figure 26:
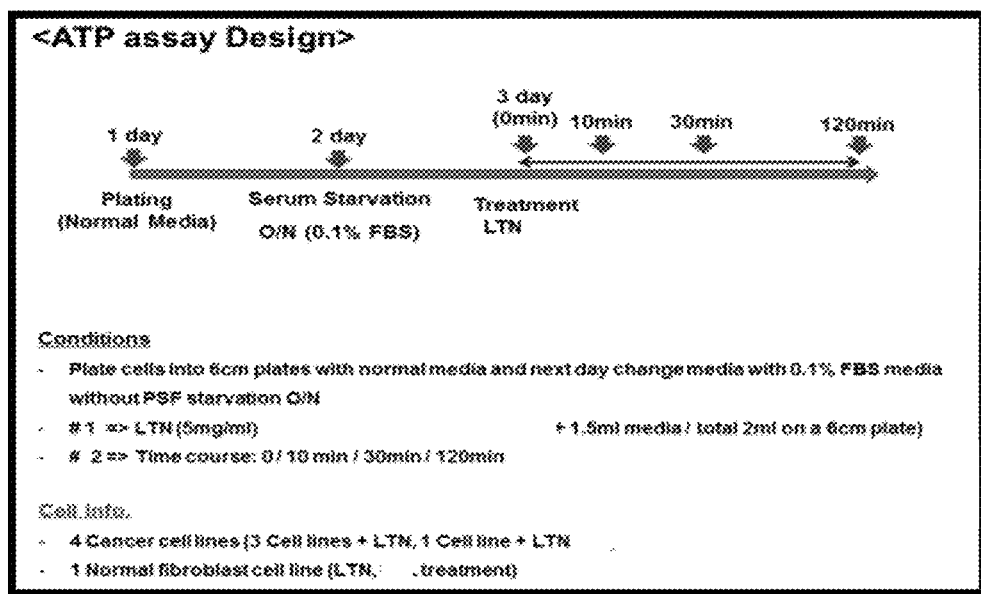
FIG. 26 is a schematic diagram of an ATP assay designed to assess the ATP production after the treatment with the luterion.

To confirm the increase of ATP production in cancer cells and Fibroblast normal cells by treatment with the luterion, $1 \times 10^6$ cells/ml of three kinds of cancer cells, A549, WTM266-4, and AsPC-1, and normal cells (MRC-5), respectively, were inoculated into 60 mm plates of normal DMEM medium, then cultured for 1 day, and then again cultured for 1 day in serum starvation using 0.1% FBS DMEM medium without antibiotic-antimycotic (PSF). On the third day therefrom, the luterion separated in Example 1 was addedat a concentration of 50 μg/ml, and then ATP production was measured at 0 minute, 10 minutes, 30 minutes, and 120 minutes, respectively (See FIG. 26). ATP measurement kit was purchased from Abcam (Cambridge, Mass., USA).

Figure 38:
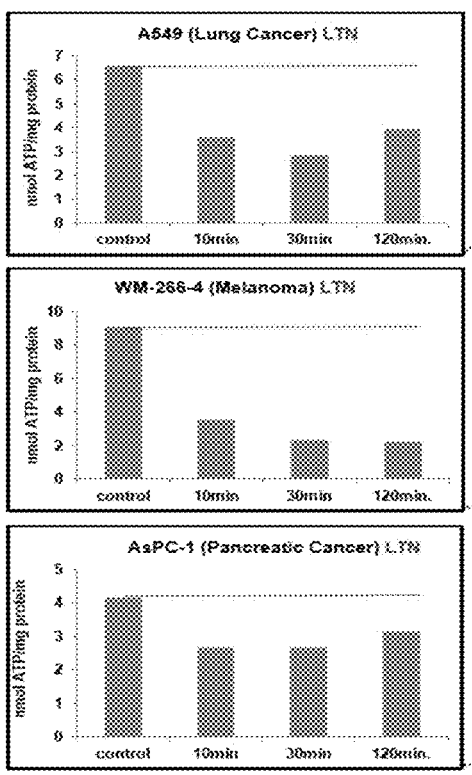
FIG. 38 shows reduction of ATP production in cancer cells by the treatment with luterion.
Figure 39:
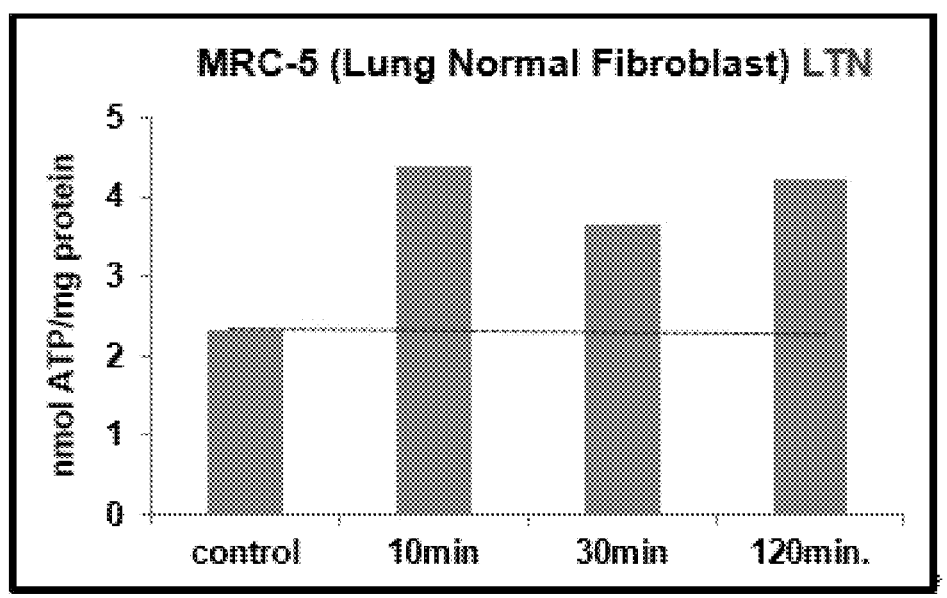
FIG. 39 shows ATP production in normal cells (Fibroblast) by the treatment with the luterion.

The results confirmed that the production of ATP remarkably increased in normal cells treated with the luterion (See FIG. 39). In addition, it was confirmed that ATP production was lowered in cancer cells treated with the luterion (See FIG. 38).

Therefore, it is found that the luterion of the present disclosure can inhibit aging by increasing energy production of normal cells. Further, it can lower the energy production of cancer cells to be applied to cancer treatment. Thus, cancer cell-specific chemotherapy can be considered without affecting the normal cells.

INDUSTRIAL APPLICABILITY

According to the present disclosure, it is possible to effectively isolate the luterion, which is a micro material present in a plant or a food and culture the separated luterion to have a predetermined size, thereby developing various uses for prevention and treatment of diseases.

As described above, the present disclosure is described in detail, but it will be apparent to those skilled in the art that this specific description is only a preferred embodiment and that the scope of the present disclosure is not limited thereby. Accordingly, the actual scope of the present disclosure will be defined by the appended claims and their equivalents.

What is claimed is:

1. A method for isolating a mitochondria-like micro-material, comprising the steps of:
   (a) filtering a condensate obtained by cooling a water vapor or gas obtained from boiling an extract of a plant or food while bubbling intermittently using a gas at 50° C. to 90° C., with a filter having a pore size of 0.8 μm to 1.2 μm;
   (b) centrifuging the filtered condensate; and
   (c) separating the mitochondria-like micro-material from a centrifuged supernatant.

2. The method according to claim 1, wherein the plant is selected from the group consisting of *angelica gigas, rhois vernicifluae cortex*, and kiwifruit.

3. The method according to claim 1, wherein boiling the extract is carried out by boiling for 8 to 10 hours and bubbling for 20 to 30 minutes every 2 to 3 hours during the boiling to prevent the mitochondria-like micro-material of the plant or food from entangling.

4. The method according to claim 1, further comprising the step of irradiating the condensate obtained in the step (a) with an infrared radiation.

5. The method according to claim 1, wherein the centrifuging in the step (b) is repeatedly performed at 1200 g to 5000 g for 5 to 10 minutes.

6. The method according to claim 1, wherein the step (c) is a step of separating the mitochondria-like micro-material by irradiating IR light having a wavelength of 200 μm to 600 μm and separating a gathered mitochondria-like micro-material having mobility or by sorting for the mitochondria-like micro-material that binds to a particle that recognizes mitochondria-like micro-material surface antigens CD39 (Cluster of Differentiation 39), CD73 (Cluster of Differentiation 73), CD133 (Cluster of Differentiation 133), or CD332 (Cluster of Differentiation 332).

7. The method according to claim 1, further comprising filtering a separated mitochondria-like micro-material with a filter having pores of less than 50 nm and then collecting an unfiltered substance trapped on the filter.

8. The method according to claim 1, further comprising a step of subjecting the mitochondria-like micro-material to a pH of 7 or lower and a temperature of 0° C. or lower.

9. The method according to claim 1, further comprising a step of subjecting the mitochondria-like micro-material to a pH of 1 to 5 and a temperature of −90° C. to 0° C.

10. The method according to claim 1, further comprising a step of inducing fission by applying a pressure of 25,000-35,000 psi (pounds per square inch).

11. The method according to claim 1, further comprising a step of proliferating the mitochondria-like micro-material by inducing fission under a pH of 1 to 3 and a temperature of 10° C. to 20° C.

12. A method of isolating a mitochondria-like micro-material, comprising the steps of: (a) adding a particle to a condensate comprising the mitochondria-like micro-material obtained by cooling a water vapor or gas obtained from boiling an extract of a plant or food while bubbling intermittently using a gas at 50° C. to 90° C., so as to induce combination of the particle and the mitochondria-like micro-material, the particle having a fixed antibody or aptamer therein, which specifically binds to a mitochondria-like micro-material surface antigen; and (b) recovering the mitochondria-like micro-material bound to the particle.

13. The method according to claim 12, further comprising a step of retrieving the mitochondria-like micro-material from the particle to which the mitochondria-like micro-material is bound.

14. The method according to claim 12, wherein the mitochondria-like micro-material surface antigen is CD39 (Cluster of Differentiation 39), CD73 (Cluster of Differentiation 73), CD133 (Cluster of Differentiation 133), or CD332 (Cluster of Differentiation 332).

* * * * *

UNITED STATES PATENT AND TRADEMARK OFFICE
CERTIFICATE OF CORRECTION

PATENT NO. : 10,569,194 B2
APPLICATION NO. : 15/542026
DATED : February 25, 2020
INVENTOR(S) : Kwon et al.

It is certified that error appears in the above-identified patent and that said Letters Patent is hereby corrected as shown below:

At page 2, Column 2, Line 4, under the heading OTHER PUBLICATIONS, in the authorship for the second cited reference, "Japazi, A." should be -- Papazi, A. --.

Signed and Sealed this
Seventh Day of April, 2020

Andrei Iancu
*Director of the United States Patent and Trademark Office*